US007648965B2

(12) United States Patent
Vignery et al.

(10) Patent No.: US 7,648,965 B2
(45) Date of Patent: *Jan. 19, 2010

(54) METHOD FOR FOSTERING BONE FORMATION AND PRESERVATION

(75) Inventors: Agnès Vignery, Branford, CT (US); Nozer M. Mehta, Randolph, NJ (US); James P. Gilligan, Union, NJ (US)

(73) Assignees: Unigene Laboratories Inc., Boonton, NJ (US); Yale University, New Haven, CT (US)

( * ) Notice: Subject to any disclaimer, the term of this patent is extended or adjusted under 35 U.S.C. 154(b) by 22 days.

This patent is subject to a terminal disclaimer.

(21) Appl. No.: 11/267,987

(22) Filed: Nov. 7, 2005

(65) Prior Publication Data

US 2006/0094656 A1    May 4, 2006

Related U.S. Application Data

(63) Continuation-in-part of application No. 11/128,095, filed on May 11, 2005.

(60) Provisional application No. 60/571,200, filed on May 14, 2004.

(51) Int. Cl.
*A61K 38/00* (2006.01)
*A61F 2/02* (2006.01)
*A61F 2/44* (2006.01)

(52) U.S. Cl. .................. 514/21; 435/810; 623/11.11; 623/13.12; 623/17.17

(58) Field of Classification Search ............... 514/21; 435/810; 623/11.11, 13.12, 17.17
See application file for complete search history.

(56) References Cited

U.S. PATENT DOCUMENTS

| | | | | |
|---|---|---|---|---|
| 3,228,393 | A | 1/1966 | Michele | 128/92 |
| 3,605,123 | A | 9/1971 | Hahn | 3/1 |
| 4,608,052 | A | 8/1986 | Van Kampen et al. | 623/22 |
| 5,108,435 | A | 4/1992 | Gustavson et al. | 623/16 |
| 5,192,324 | A | 3/1993 | Kenna | 623/16 |
| 5,263,986 | A | 11/1993 | Noiles et al. | 623/16 |
| 5,358,533 | A | 10/1994 | Noiles et al. | 623/22 |
| 5,441,537 | A | 8/1995 | Kenna et al. | 419/2 |
| 5,489,306 | A | 2/1996 | Gorski | 623/16 |
| 5,510,370 | A | 4/1996 | Hock | 514/443 |
| 5,789,234 | A | 8/1998 | Bertelsen et al. | 435/240.2 |
| 6,103,495 | A | 8/2000 | Mehta et al. | 435/69.1 |
| 6,319,685 | B1 | 11/2001 | Gilligan et al. | 435/68.1 |
| 6,362,231 | B1 | 3/2002 | Sakai et al. | 514/654 |
| 6,376,476 | B1 | 4/2002 | Gasper et al. | 514/100 |
| 6,395,919 | B1 | 5/2002 | Bhatnagar et al. | 558/414 |
| 6,432,656 | B1 | 8/2002 | Del Mar et al. | 435/7.21 |
| 6,521,667 | B1 | 2/2003 | Del Mar et al. | 514/653 |
| 6,620,332 | B2 | 9/2003 | Amrich | 216/11 |
| 6,682,567 | B1 | 1/2004 | Schroeder | 623/22.24 |
| 6,758,849 | B1 | 7/2004 | Michelson | 606/61 |
| 7,531,518 | B2 | 5/2009 | Vignery et al. | |
| 2004/0033950 | A1 | 2/2004 | Hock et al. | 514/12 |

FOREIGN PATENT DOCUMENTS

WO    WO 03/039331    5/2003
WO    WO 2005/011286    12/2005

OTHER PUBLICATIONS

U.S. Appl. No. 11/254,640, filed Oct. 21, 2005, Murphy et al.
U.S. Office Action (from U.S. Appl. No. 11/128,095) with mailing date of Oct. 31, 2007.
U.S. Appl. No. 11/839,957, filed Aug. 16, 2007, Agnes Vignery et al.
U.S. Appl. No. 11/839,993, filed Aug. 16, 2007, Agnes Vignery et al.
Voelker, *JAMA* (1998), vol. 280, p. 315.
International Search Report dated Sep. 22, 2006.
U.S. Appl. No. 11/128,095, filed May 11, 2005, Vignery et al.
U.S. Appl. No. 11/430,752, filed May 9, 2006, Vignery et al.
Whitfield et al., "Parathyroid Hormone, Its Fragments and Their Analogs for the Treatment of Osteoporosis", *Treatment in Endocrinology*, 2002, 1(3):175-19.
Skripitz, et al., "Strong Effect of PTH (1-34) on Regenerating Bone", *ACTA Orthop. Scand.*, 2000, 71 (6): 619-624.
Reginster et al., "Strontium Ranelate: A New Paradigm in the Treatment of Osteoporosis", *Expert Opin. Investig. Drugs*, 2004, vol. 13, No. 7, pp. 857-864.
Suva, et al., "Pattern of Gene Expression Following Rat Tibial Marrow Ablation", *Journal of Bone and Mineral Research*, 8(3):379-388 (1993).
Shimizu, et al., "Sequential Expression of Bone Morphogenetic Protein, Tumor Necrosis Factor, and Their Receptors in Bone-Forming Reaction After Mouse Femoral Marrow Ablation", *Bone*, 23(2):127-133 (1998).
Yamashita, et al., "Retardation in Bone Resorption after Bone Marrow Ablation in *Klotho* Mutant Mice", *Endocrinology*, 141(1):438-445 (2000).
Tanaka, et al., "Local and Systemic Expression of Insulin-like Growth Factor-I (IGF-I) mRNAs in Rat after Bone Marrow Ablation", *Biochemical and Biophysical Research Communications*, 287(5):1157-1162 (2001).

(Continued)

*Primary Examiner*—Jon P Weber
*Assistant Examiner*—Abdel A Mohamed
(74) *Attorney, Agent, or Firm*—Ostrolenk Faber LLP

(57) ABSTRACT

A method of inducing bone formation in a subject in need of such inducement comprises the steps of mechanically inducing an increase in osteoblast activity in the subject and elevating blood concentration of at least one bone anabolic agent in the subject. The method steps may be performed in any order, but in sufficient time proximity that the elevated concentration of the anabolic agent and the mechanically induced increase in osteoblast activity overlaps. The method may additionally comprise providing the subject with an elevated blood concentration of at least one antiresorptive agent, wherein the elevated concentration is sufficient to prevent resorption of new bone growth produced due to the osteoblast activity. Use of the method permits targeting of specific bones of the subject for bone production and preservation, faster bone production and earlier discontinuation of bone anabolic pharmaceuticals. Kits adapted for performing the method are provided.

62 Claims, 19 Drawing Sheets

OTHER PUBLICATIONS

Tanaka, et al., "Effect of IGF-I and PDGF administered in vivo on the expression of osteoblast-related genes in old rats", *Journal of Endocrinology*, 174(1):63-70 (2002).

Tanaka, et al., "Effects of basic fibroblast growth factor on osteoblast-related gene expression in the process of medullary bone formation induced in rat femur", *Journal of Bone and Mineral Metabolism*, 21:74-79 (2003).

Chen, et al., "Biglycan-Deficient Mice Have Delayed Osteogenesis after Marrow Ablation", *Calcified Tissue International*, 72(5):577-582 (2003).

Andreassen, et al., "Intermittent Parathyroid Hormone (1-34) Treatment Increases Callus Formation and Mechanical Strength of Healing Rat Fractures", *Journal of Bone and Mineral Research*, 14:960-968 (1999).

Nakajima, et al., Mechanisms for the Enhancement of Fracture Healing in Rats Treated With Intermittent Low-Dose Human Parathyroid Hormone (1-34), *Journal of Bone and Mineral Research*, 17:2038-2047 (2002).

U.S. Appl. No. 12/059,662, filed Mar. 31, 2008, Agnes Vignery et al.

U.S. Appl. No. 11/430,752, filed May 9, 2006, Agnes Vignery et al.

Hunziker, J. et al., "Mandibular bone formation rates in aged ovariectomized rats treated with anti-resorptive agents alone and in combination with intermittent parathyroid hormone", Journal of Dental Research, vol. 79, No. 6, Jun. 2000, pp. 1431-1438.

Nemeth, E. et al., "Calcilytic compounds: Potent and selective Ca2+ receptor antagonists that stimulate secretion of parathyroid hormone", Journal of Pharmacology and Experimental Therapeutics, vol. 299, No. 1, Oct. 2001, pp. 323-331.

Skripitz et al., "Implant fixation enhanced by intermittent treatment with parathyroid hormone", Journal of Bone and Joint Surgery, British Volume, Livingstone, London GB, vol. 83-B, No. 3, Apr. 2001, pp. 437-440.

Skripitz, R. et al., "Parathyroid hormone increases attachment of PMMA cement to bone", Journal of Orthopaedic Science: Official Journal of the Japanese orthopaedic Association 2001, vol. 6, No. 6, 2001, pp. 540-544.

Kobayashi, S. et al., "Advantages of concurrent use of anabolic and antiresorptive agents over single use of these agents in increasing trabecular bone volume, connectivity and biomechanical competence of rat vertebrae", Bone, vol. 25, No. 6, Dec. 1999, pp. 703-712.

Supplementary European Search Report dated Aug. 25, 2009 corresponding to European Patent Application No. 05760624.6.

Extended European Search Report dated Sep. 14, 2009 corresponding to European Patent Application No. 05851371.4.

Left femur (a)

Right femur (b)

METHOD FOR FOSTERING BONE FORMATION AND PRESERVATION

CROSS-REFERENCE TO RELATED APPLICATIONS

This application is a continuation-in-part of application Ser. No. 11/128,095 filed May 11, 2005 which, in turn, is based on and claims the priority of Provisional Application No. 60/571,200 which was filed May 14, 2004, the contents of which are specifically incorporated herein.

STATEMENT REGARDING FEDERALLY SPONSORED RESEARCH OR DEVELOPMENT

The invention disclosed herein was made with Government support under NIH Grant No. DE 12110 from the National Institutes of Health. Accordingly, the government has certain rights in this invention.

FIELD OF THE INVENTION

The present invention relates generally to a method for fostering bone formation in a subject. More particularly the invention concerns a method for inducing rapid bone formation and then preserving the bone thus produced, e.g., by minimizing its resorption. The invention permits specific targeting of particular bones of a subject for repair, strengthening, reshaping and/or modeling. The invention is additionally directed to a kit for carrying out the method of the invention.

BACKGROUND OF THE INVENTION

Bones are multi-purpose structures that play diverse, vital roles in vertebrates. They provide a framework that supports the body and gives it shape. Bone undergoes a continuous renewal or remodeling during the lifetime of an individual. Bone consists of living cells widely scattered within a non-living material known as matrix. Two main types of cells are responsible for bone remodeling: the osteoblasts involved in bone formation and the osteoclasts involved in bone resorption. The matrix is formed by the action of osteoblasts, that make and secrete bone matrix proteins such as collagen, which provide elasticity, as well as mineral salts formed from calcium and phosphorous, which impart hardness to bone. As bone tissue matures, some osteoblasts are trapped in the bone matrix and differentiate into osteocytes, which are mature bone cells that carry out normal cellular activities. These osteocytes connect with other osteocytes through the bone matrix and can sense pressure or cracks in the bone. They therefore assist in directing where osteoclasts will act to resorb bone during the repair and/or regeneration of bone.

Osteoclasts are cells that resorb existing bone, thus facilitating bone growth, repair and regeneration. Osteoclasts are multinucleated cells that originate from the fusion of mononuclear phagocytes. Osteoclasts secrete protons that lower the pH of an extracellular compartment located between osteoclasts and bone. This low pH facilitates the dissolution of bone crystals and activates lysosomal enzymes that digest the bone matrix. Osteoclasts are therefore powerful and efficient bone resorbing cells that cover only 0.5% of the bone surface. With regard to bone formation, osteoblasts produce a structure, known as "osteoid", which is formed of bone collagen and other proteins. The osteoblasts thereafter control the deposition of calcium and other minerals into the osteoid in order to produce the calcified bone tissue. Upon the completion of bone formation, the osteoblasts flatten out and form a lining upon the surface of the bone. These flattened osteoblasts, known as "lining cells", regulate passage of calcium into and out of the bone. In addition, they produce, upon hormonal activation, proteins that promote osteoblast differentiation and activation. Making new bone is therefore a slow process that requires the lying down of the osteoid, its maturation and then its calcification. In contrast to osteoclasts, osteoblasts cover 30% of the bone surface.

The bones of the skeleton are not entirely solid throughout. The outside, i.e., cortical, bone is substantially solid throughout, having only a few small canals. Located inwardly from the cortical bone, however, is spongy bone known as cancellous bone. The cancellous bone is composed of a honeycomb network of trabecular bone defining a plurality of spaces or cavities filled with fluid bone marrow, stem cells and some fat cells. Existing within these bone marrow cavities are, inter alia, various highly specialized cells which assist in breaking down existing bone and correspondingly producing new bone to replace that which is broken down or which may be otherwise lost due to injury or illnesses such as osteoporosis.

The physical structure of bone may be compromised by a variety of factors, including disease and injury. One of the most common bone diseases is osteoporosis, which is characterized by low bone mass and structural deterioration of bone tissue, leading to bone fragility and an increased susceptibility to fractures, particularly of the hip, spine and wrist. Osteoporosis develops when there is an imbalance such that the rate of bone resorption exceeds the rate of bone formation. This is in part due to the fact that it requires six months for osteoblasts to rebuild the amount of bone destroyed by osteoclasts in three days. Bone injury, on the other hand, involves localized trauma to the bone.

A variety of methods are well-known in the art for fostering bone formation in individuals who (1) suffer from diminished bone mass due, for example, to illness, (2) are subjected to bone trauma causing injury such as bone fractures, and (3) need to strengthen bone, such as vertebral bones. Such prior art methods for treating these disorders are typically systemic in nature, however. That is, they treat the whole skeleton as a single entity. These methods are therefore not commonly able to be targeted on one or more specific bones, e.g., those of the hip, shoulder, spine and/or wrist, which may require a more focused treatment due to bone losses due to disease effects caused by, e.g., osteoporosis or by bone trauma such as that due to a fracture. Moreover, prior art methods frequently require undesirably long treatment regimens, with accompanying patient compliance problems.

There has thus been a long-felt need by those working in this field for a faster and more targeted method of inducing bone formation in subjects suffering from diminished bone mass, especially for a method coupled with an enhancement in retention of the new bone so produced. The present invention permits, in addition to the general systemic effect noted above, specific targeting of one or more particular bones or bony areas most in need of such treatment for rapid bone formation. As explained below, the method and kit of the present invention are particularly adapted to provide more effective bone formation with increased rapidity while permitting the retention of the bone thus produced and thus to admirably fulfil the desired functions.

SUMMARY OF THE INVENTION

It is therefore an object of the present invention to provide a method for inducing rapid bone formation in a subject such that the length of treatment with a bone anabolic agent may be reduced, thus offering safety and pharmacoeconomic advantages.

It is also an object of the present invention to provide a method for inducing bone formation at a rapid rate in a subject suffering from diminished bone mass, which method permits specific bones of the subject to be targeted for an increase in bone mass, while additionally providing beneficial bone formation effects to the entire skeleton of the subject.

It is another object of the invention to provide a method capable of inducing rapid bone formation in subjects so as to prevent and/or treat bone fractures.

It is a further object of the invention to provide a method capable of inducing rapid bone formation in subjects requiring such additional bone to serve as an anchoring mechanism for prostheses of, e.g., the hip, knee and shoulder and/or other types of implants such as dental implants.

It is a still further object of the invention to provide a method capable of inducing rapid bone formation in subjects requiring bone strengthening to alleviate chronic pain due to conditions such as vertebral crush.

It is yet another object of the invention to provide a method capable of diminishing resorption of any substantial portion of such additional bone thus produced in accordance with the invention.

It is another object of the invention to provide a method capable of inducing rapid bone formation so as to permit bone reshaping/modeling via said additional bone formation.

It is a further object of the invention to provide an article of manufacture comprising a kit adapted to enable one to carry out the above-described method of the invention.

In a preferred embodiment, the method of the invention is utilized with a human subject. However, the invention additionally contemplates veterinary applications.

In one embodiment, the invention provides a method of inducing bone formation in a subject in need of such inducement comprising the steps of (a) mechanically inducing an increase in osteoblast activity in the subject; and (b) elevating blood concentration of at least one bone anabolic agent therein, e.g., by administering such an agent or by administering a compound which causes natural formation of such an agent. The aforesaid steps may be performed in any order, but in sufficient time proximity that the elevated concentration of the anabolic agent and the mechanically induced increase in osteoblast activity at least partially overlaps.

In a further embodiment of the invention the method comprises the steps of targeting for treatment at least one bone of the subject, wherein each such targeted bone defines a bone marrow cavity therein. The bone marrow cavity contains, inter alia, a quantity of bone marrow and a plurality of osteoblasts. The method further comprises mechanically altering the contents of the bone marrow cavity to thereby stimulate and thus increase osteoblast differentiation and/or activity therein. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The mechanical alteration of the contents of the bone marrow cavity in bones wherein it is desired to foster such bone growth permits specific bones of the subject to be particularly targeted for inducing bone formation therein.

The invention further provides a method of inducing bone formation in a subject suffering from diminished bone mass which comprises the steps of targeting for treatment at least one bone of the subject, wherein each targeted bone defines a bone marrow cavity therein. The bone marrow cavity contains a quantity of bone marrow and a plurality of osteoblasts. The method of the invention further comprises mechanically altering the contents of the bone marrow cavity to thereby stimulate and thus increase osteoblast activity (e.g., increased differentiation or increased bone formation by stimulating osteoblasts) therein. Thereafter, bone mass is increased within the cavity due to the increased osteoblast activity. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The method, however, further comprises additionally administering, either (1) contemporaneous with, (2) overlapping with, or (3) subsequent to the administration of the bone anabolic agent, an antiresorptive agent for a duration and at a concentration sufficient to diminish resorption of new bone produced due to the osteoblast activity. As with the method described above, the mechanical alteration of the contents of the bone marrow cavity of bones in which such stimulated growth is desired thus permits specific bones of the subject to be particularly targeted for enhanced bone formation.

The invention further provides a method for inducing bone formation within a bone of a subject which comprises mechanically altering the contents of a bone marrow cavity within said bone to thereby stimulate, and thus increase, osteoblast differentiation activity therein so as to induce bone growth therein. The method further comprises administering to said subject an amount of an anti-resorptive agent for a time and at a concentration sufficient to substantially prevent resorption of the new bone produced due to the osteoblast activity. The anti-resorptive agent, which may be but is not necessarily salmon calcitonin, may be administered contemporaneous with the mechanical alteration and/or subsequent thereto. This method does not include the administration of a bone anabolic agent The invention additionally provides a kit for fostering bone formation in at least one targeted bone of a subject in need of such bone formation. In one embodiment, the kit includes at least one container having therein at least one bone anabolic agent, as well as a mechanical alteration device for altering contents of a bone marrow cavity in at least one targeted bone. In another embodiment the kit may include at least one container having therein at least one bone anti-resorptive agent, as well as a mechanical alteration device for altering contents of the bone marrow cavity of a selected bone. In a still further embodiment, the kit may include multiple containers with at least one bone anabolic agent and at least one bone anti-resorptive agent, as well as the mechanical alteration device described above. In any event, the kit may additionally be provided with an evacuation device for evacuating at least a portion of the contents from the bone marrow cavity.

BRIEF DESCRIPTION OF THE DRAWING(S)

FIG. 1 is a graphical representation of the results of a PIXIMUS analysis of the femur distal marrow cavity bone mineral density ("BMD") of groups of laboratory rats which were sacrificed at one-week intervals during a three-week test regimen. The PIXIMUS analyzer is available from Lunar Corp., Palo Alto, Calif. and provides Dual Energy X-Ray Absorptiometry ("DEXA") data for small animals such as mice and rats. Male Sprague-Dawley rats (5 animals per group) aged 9 weeks were sacrificed and tested at time 0 and after 1, 2 and 3 weeks. The various groups were subjected to the following treatment modalities: Group A—left femur control; Group B—left femur sham; Group C—mechanical bone marrow ablation (bmx) to alter the contents of the bone marrow cavity of the left femur; Group D—mechanical bone marrow ablation treatment (bmx) of the left femur, coupled with the administration of an amidated parathyroid hormone truncate (PTH[1-34]-NH$_2$) during days 1-21; and Group E—a right (non-bmx) femur BMD measurement of rats treated during days 1-21 with an amidated parathyroid hormone truncate (PTH[1-34]-NH$_2$) wherein the rat's left femur had undergone a bone ablation (bmx) treatment;

FIG. 2 is a graphical representation of the results of a PIXIMUS analysis of the femur distal marrow cavity BMD of a second set of groups of male Sprague-Dawley rats (5 animals per group) aged 9 weeks which were sacrificed and tested at time 0 and after 1, 2 and 3 weeks. The various groups were subjected to the following treatment modalities: Group F—left femur control; Group G—left femur sham; Group H—mechanical bone marrow ablation (bmx) to alter the contents of the bone marrow cavity of the left femur; Group I—mechanical bone marrow ablation (bmx) of the left femur, coupled with administration of an amidated parathyroid hormone truncate (PTH[1-34]-NH$_2$) during days 1-7, followed by the administration of a salmon calcitonin (sCT) antiresorptive agent during days 7-21; and Group J—a right femur BMD measurement of rats treated with an amidated parathyroid hormone truncate (PTH[1-34]-NH$_2$) wherein the rat's left femur had undergone a bone marrow ablation (bmx) treatment;

FIGS. 3 (a-e) present high resolution radiograms of, respectively, the left (ablated) and right (non-ablated) femurs of some of the rats described with regard to FIGS. 1 and 2 above. (See discussion below of Tables 1 and 2) The radiographs were taken three weeks (i.e., 21 days) following commencement of treatment. The rats were treated as follows: (a) control (i.e., no surgery); (b) sham (i.e., surgery without marrow ablation); (c) mechanical bone marrow ablation (bmx)+ phosphate buffer saline (PBS) administration daily for 21 days; (d) bmx followed by parathyroid hormone (PTH[1-34]-NH$_2$) administered daily for 21 days; and (e) bmx followed by parathyroid hormone (PTH[1-34]-NH$_2$) administered daily for 7 days and then salmon calcitonin given daily from days 7-21. A marking of bmx with regard to a right (non-ablated) femur means that the marrow of the contralateral left femur from the same rat has been ablated. This usage will be followed throughout;

FIGS. 4 (a-d) are graphical representations of the results of Peripheral Quantitative Computerized Tomography (PQCT) analyses of, respectively, the left (ablated) and right (non-ablated) femoral shafts of the rats which are the subject of FIG. 3 above. FIGS. 4(a) and 4(b) illustrate the trabecular bone density observed in respectively, the left and right femoral shafts of these rats, whereas, FIGS. 4(c) and 4(d) illustrate the total bone density of the respective shafts. The meanings of the abbreviations used in FIGS. 4a-4d are identical to those described above with regard to FIGS. 3 (a-e);

FIG. 5 provides a series of measurements of the serum osteocalcin concentration (in ng/ml) in the blood of the rats which are the subjects of FIGS. 3-4 on the day of sacrifice. The meaning of the abbreviations is the same as that in FIGS. 3-4;

Figure 8:
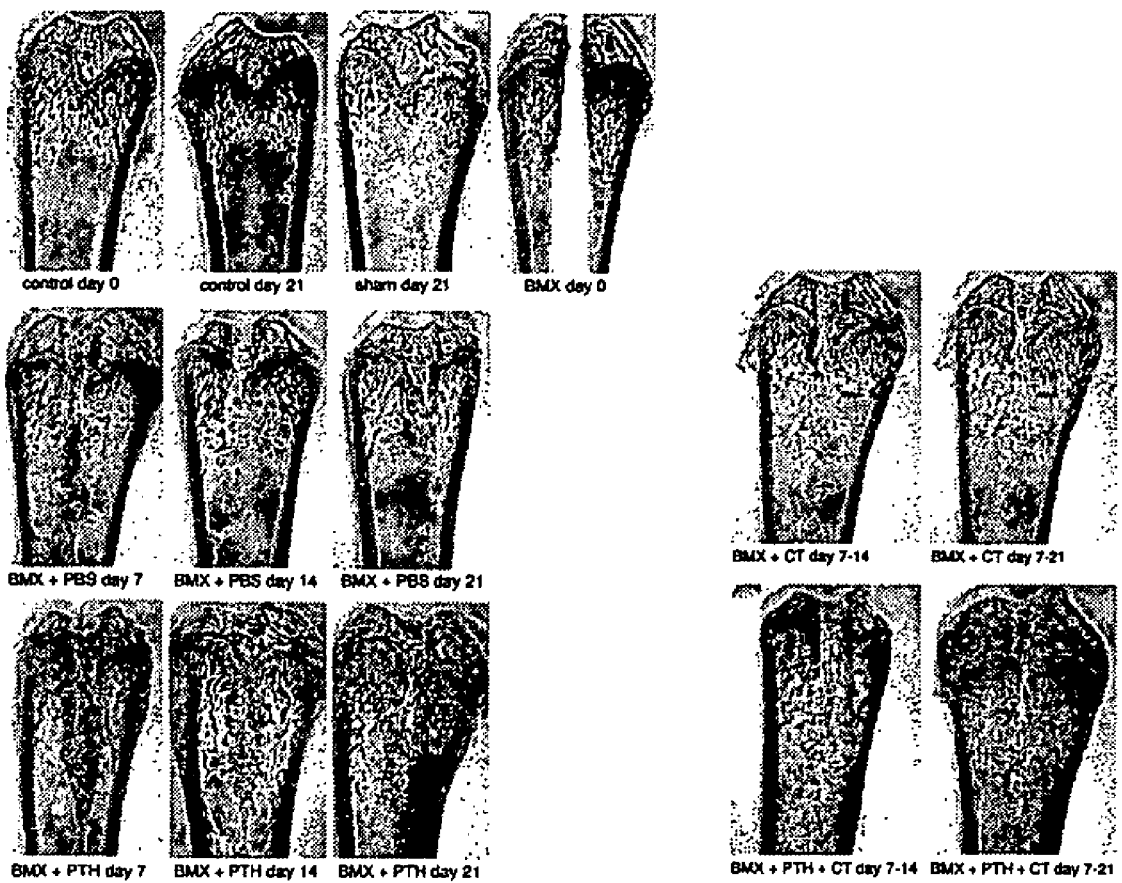
FIG. 8 illustrates sections (at 4× magnification) of undecalcified left femurs, subjected to bone marrow ablation (bmx), wherein the bone sections were stained with Von Kossa stain.
Figure 9:
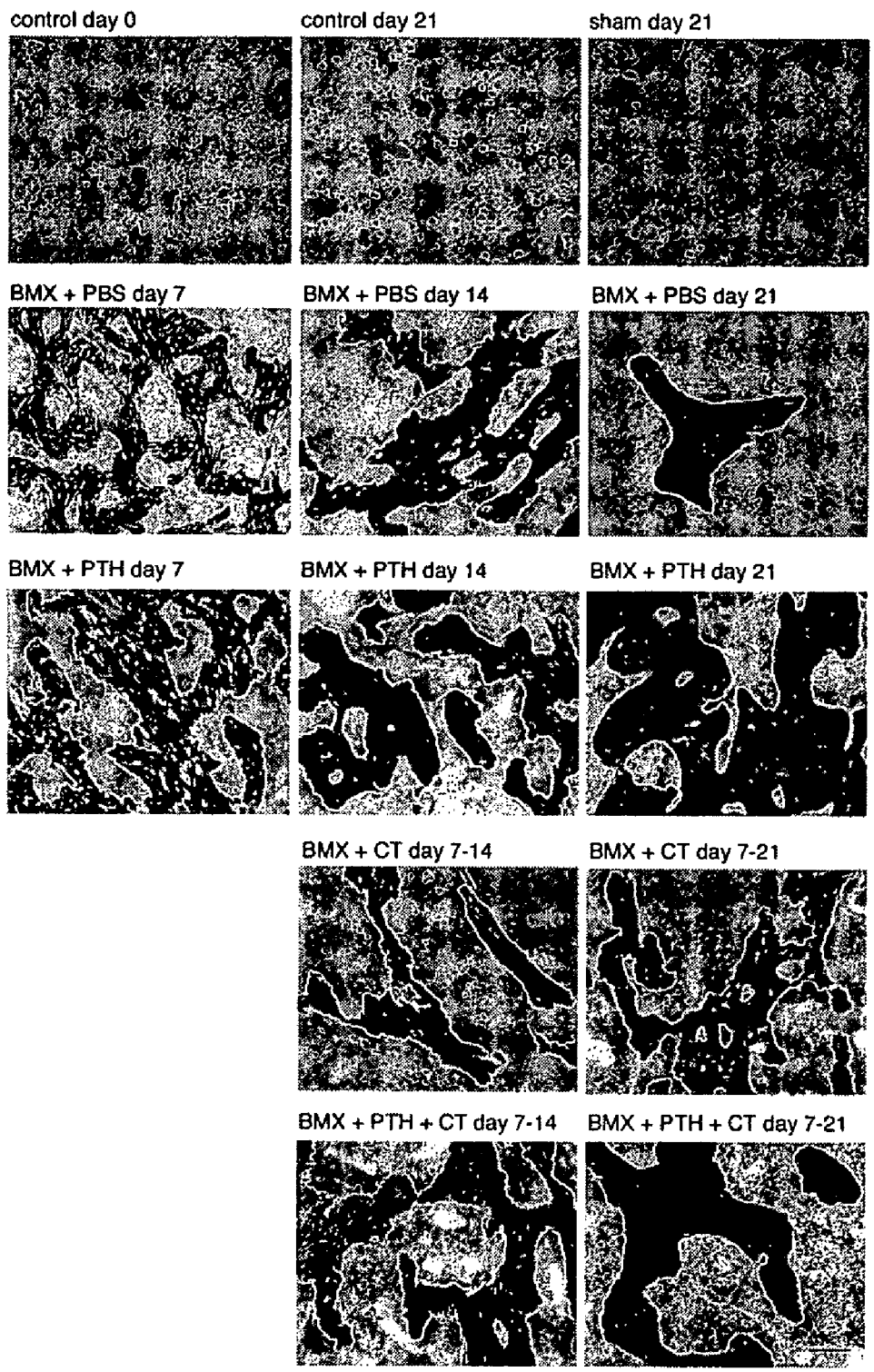
Figure 10:
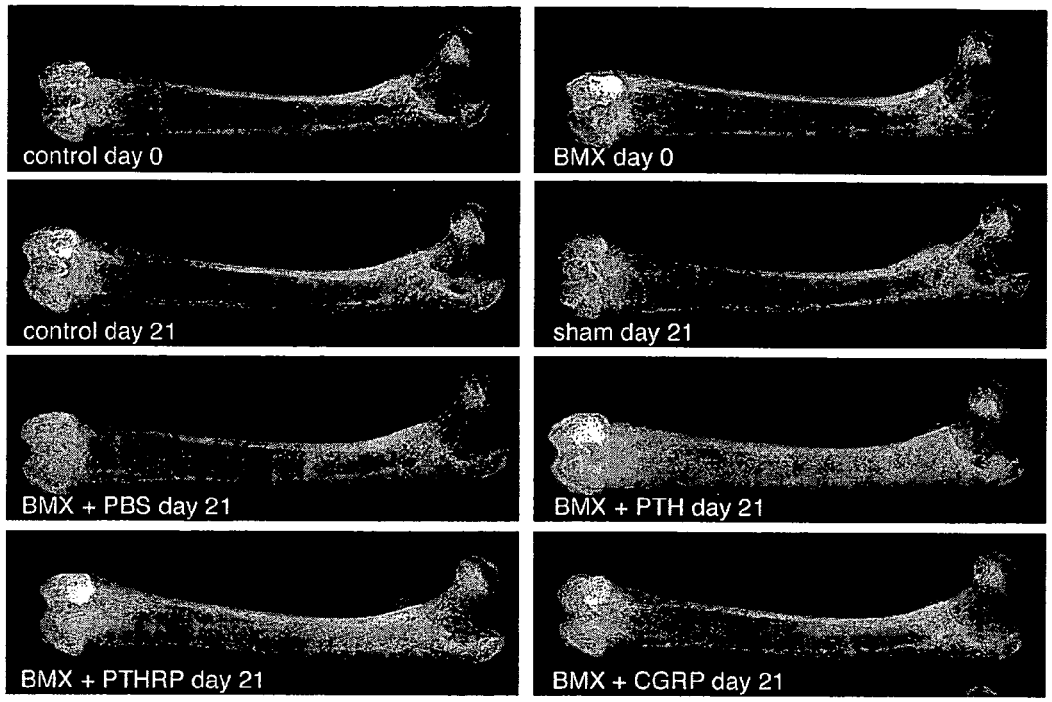
Figure 10:
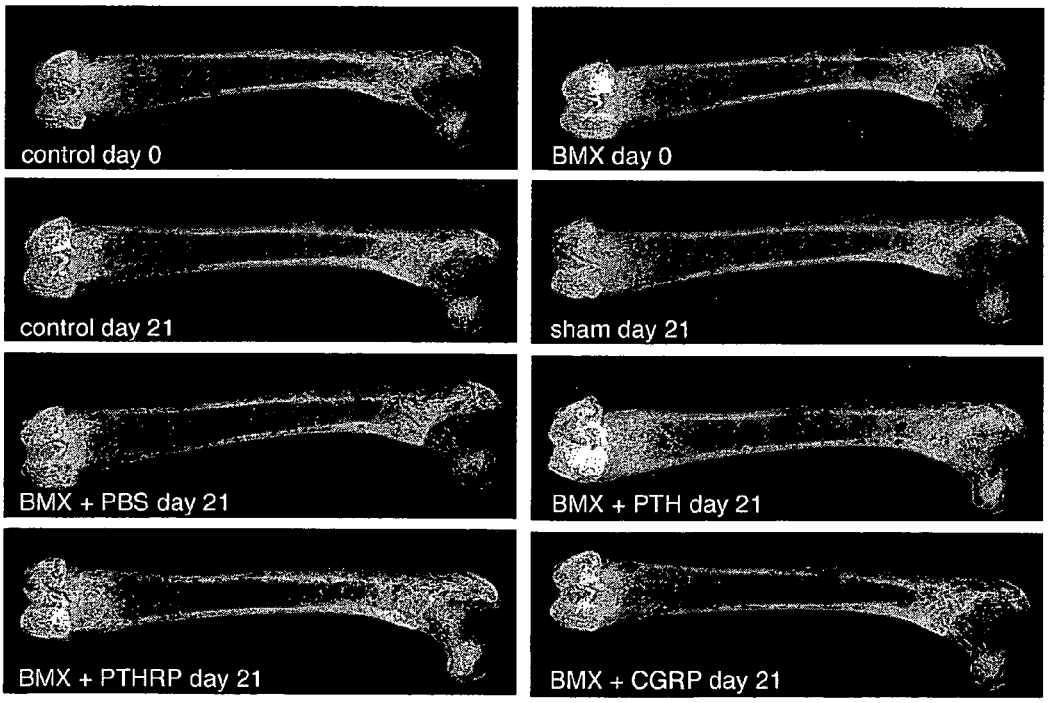
Figure 11:
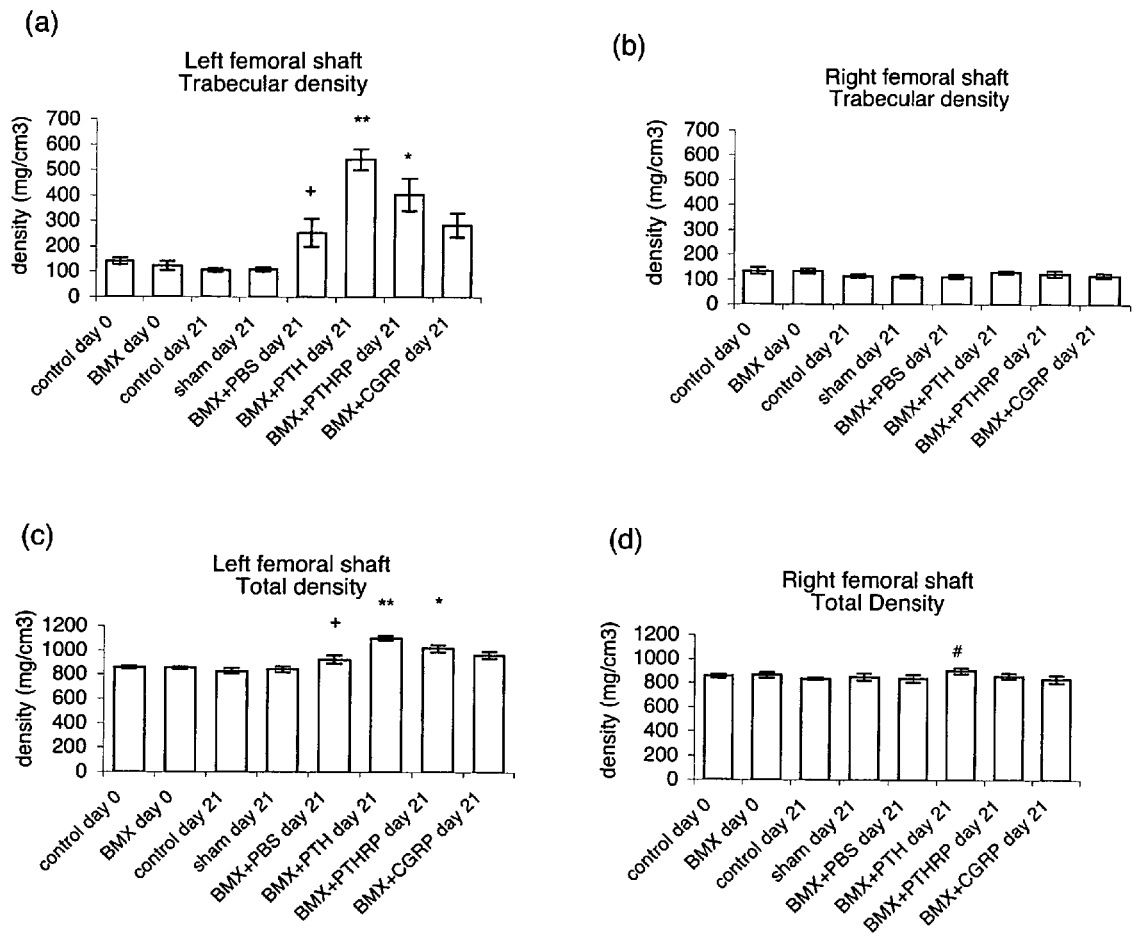
Figure 12:
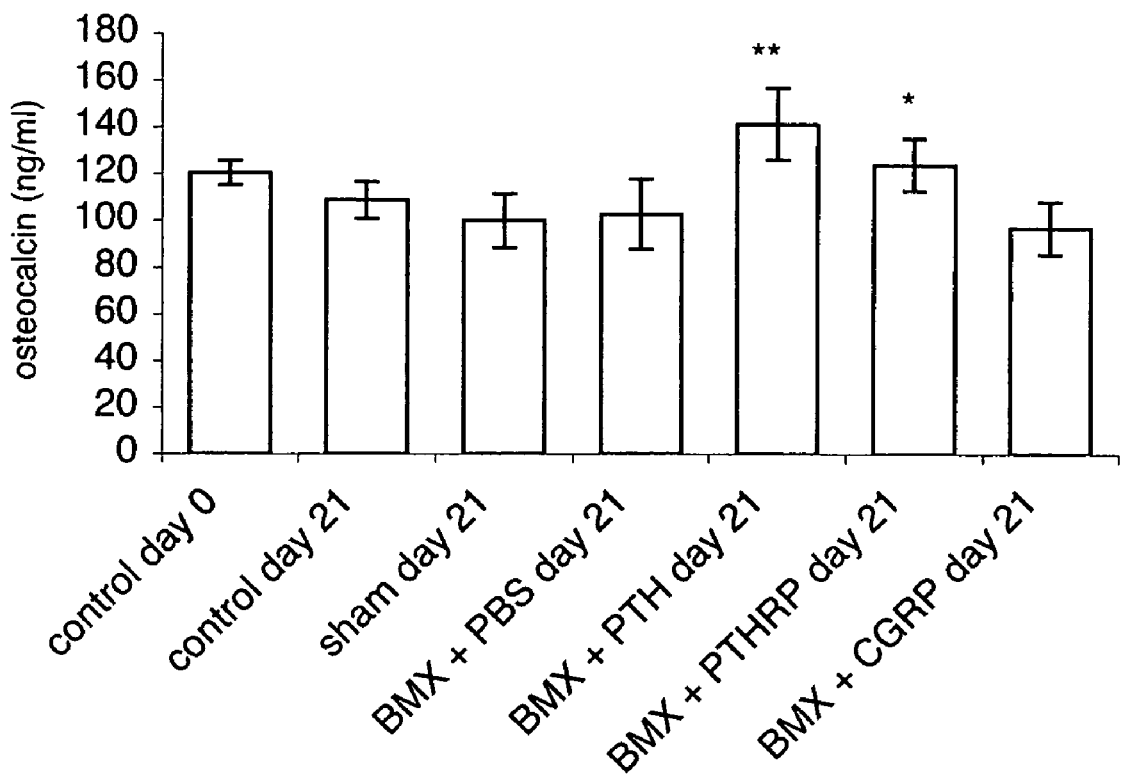
Figure 13:
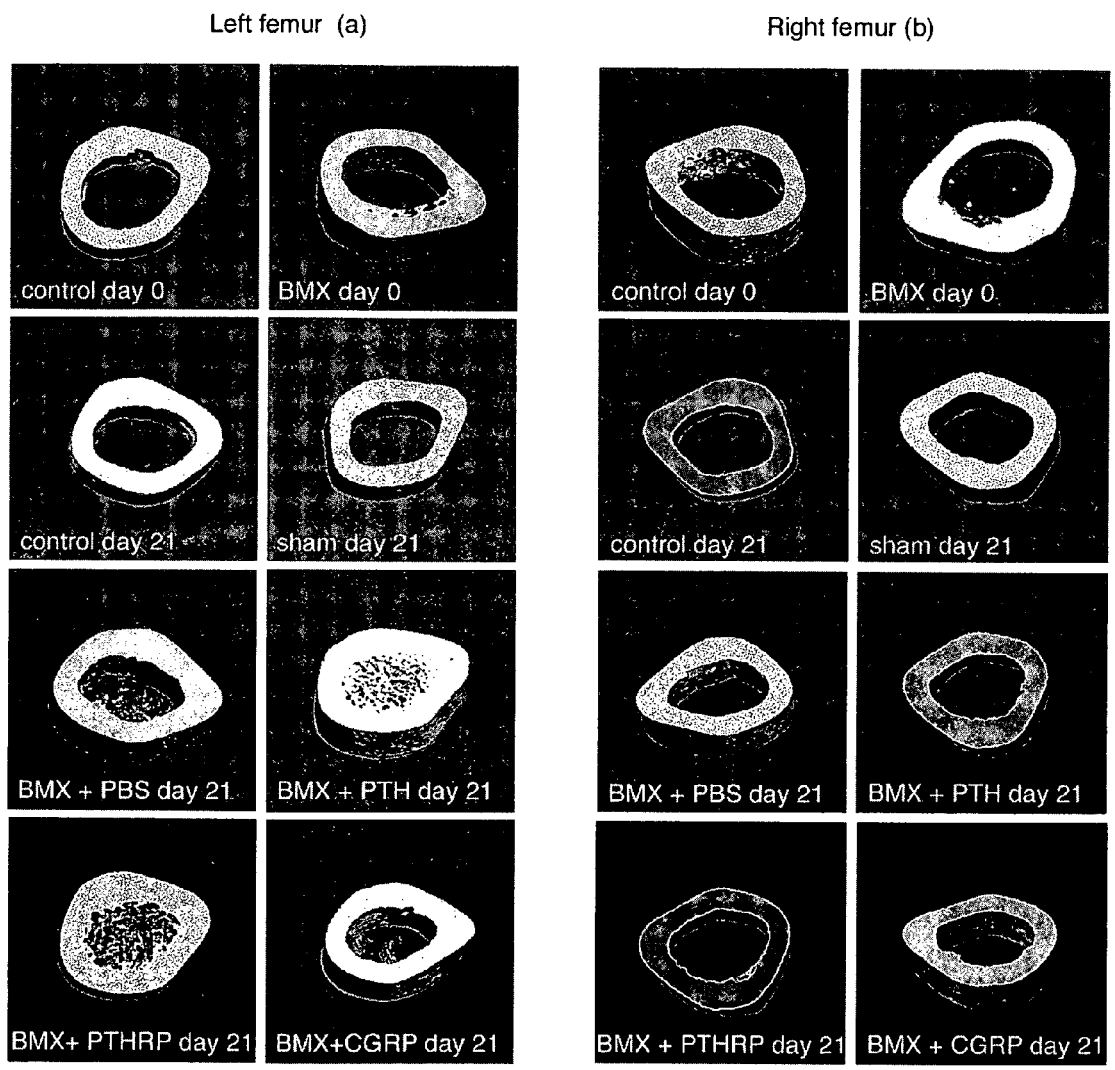
Figure 14:
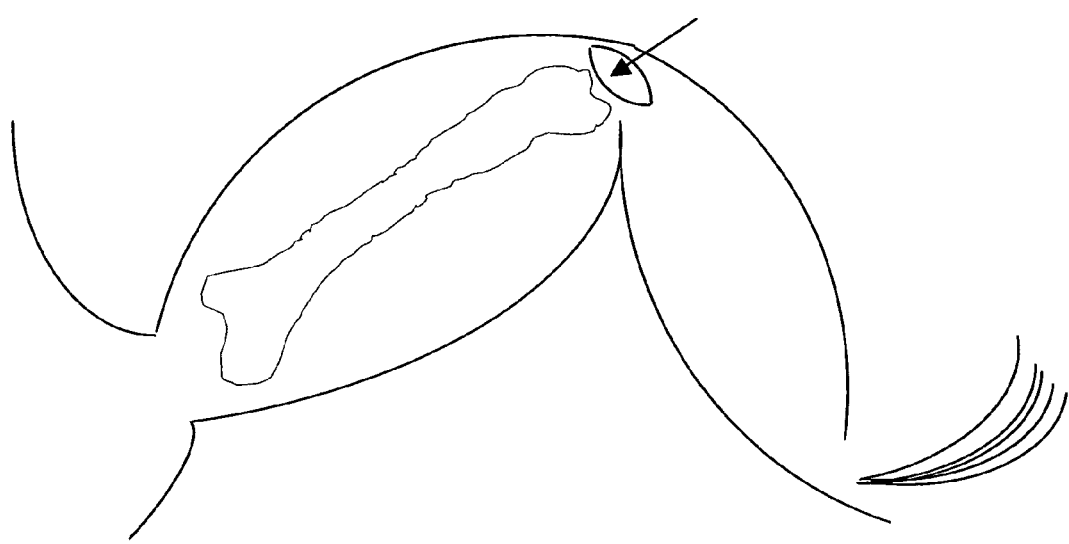
Figure 14:
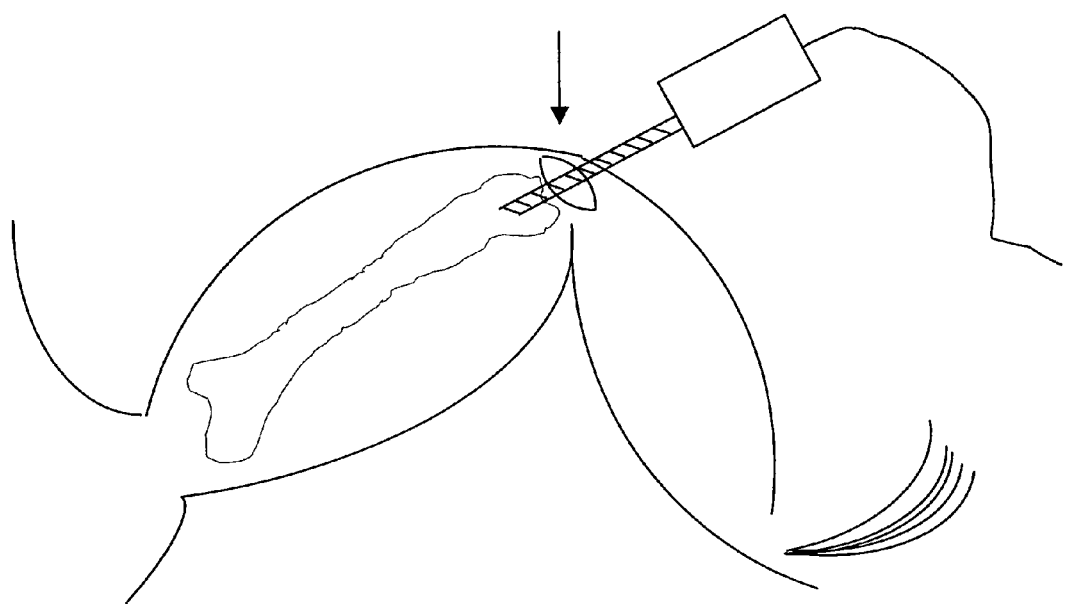
Figure 14:
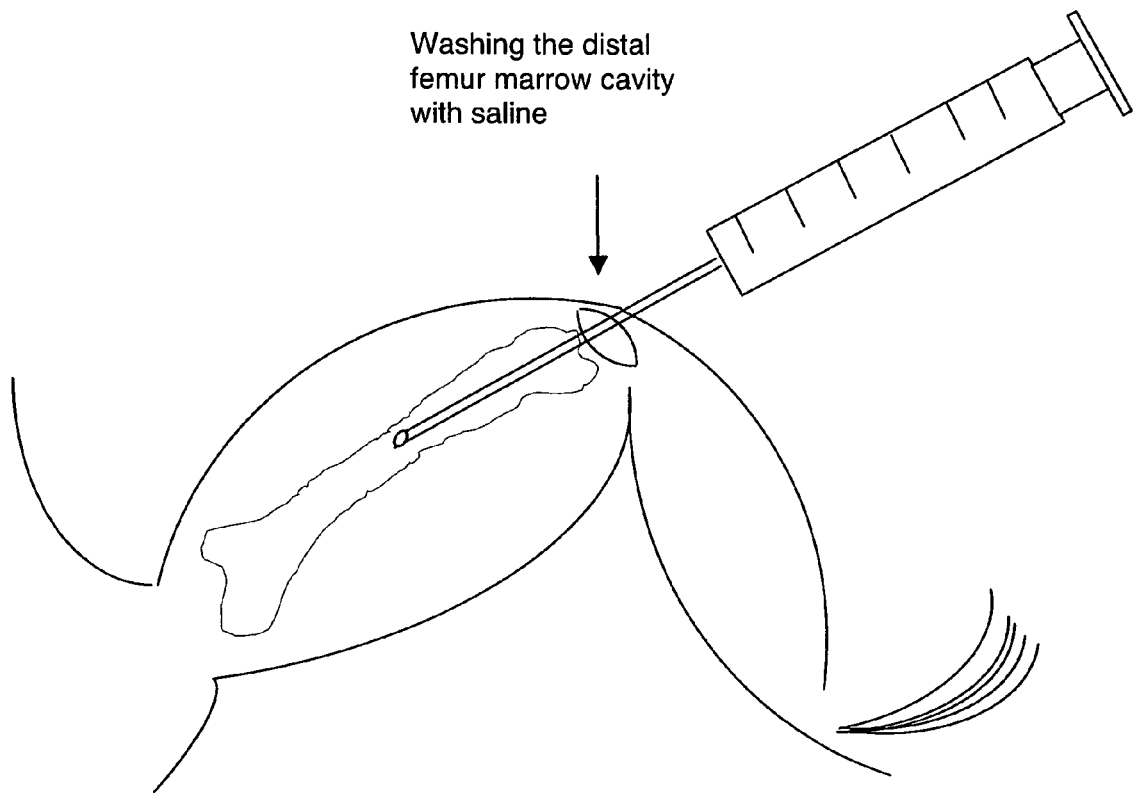
Figure 14:
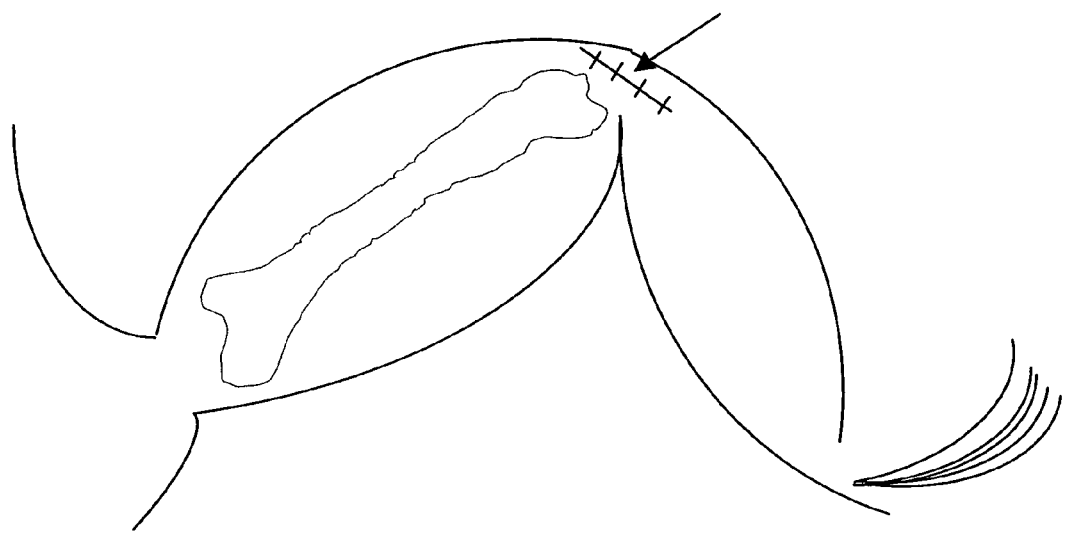
Figure 15:
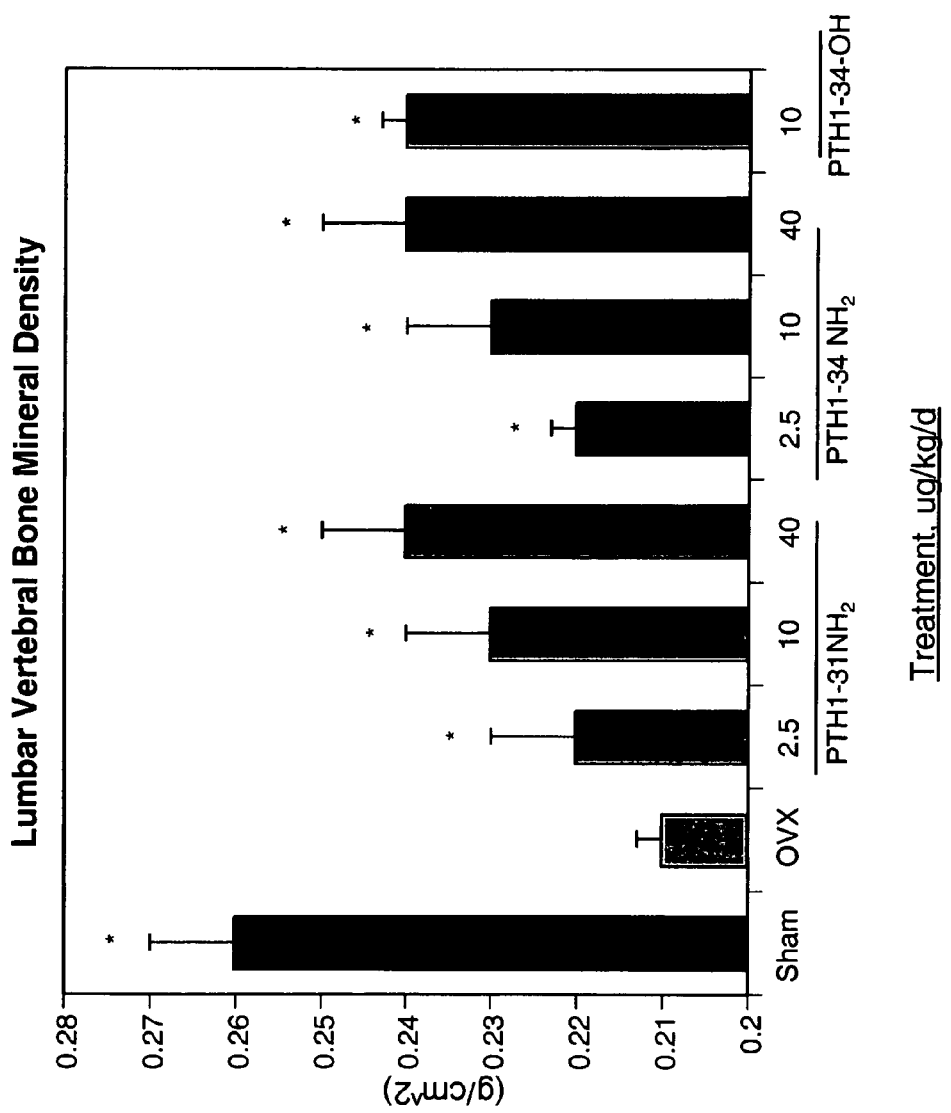
Figure 16:
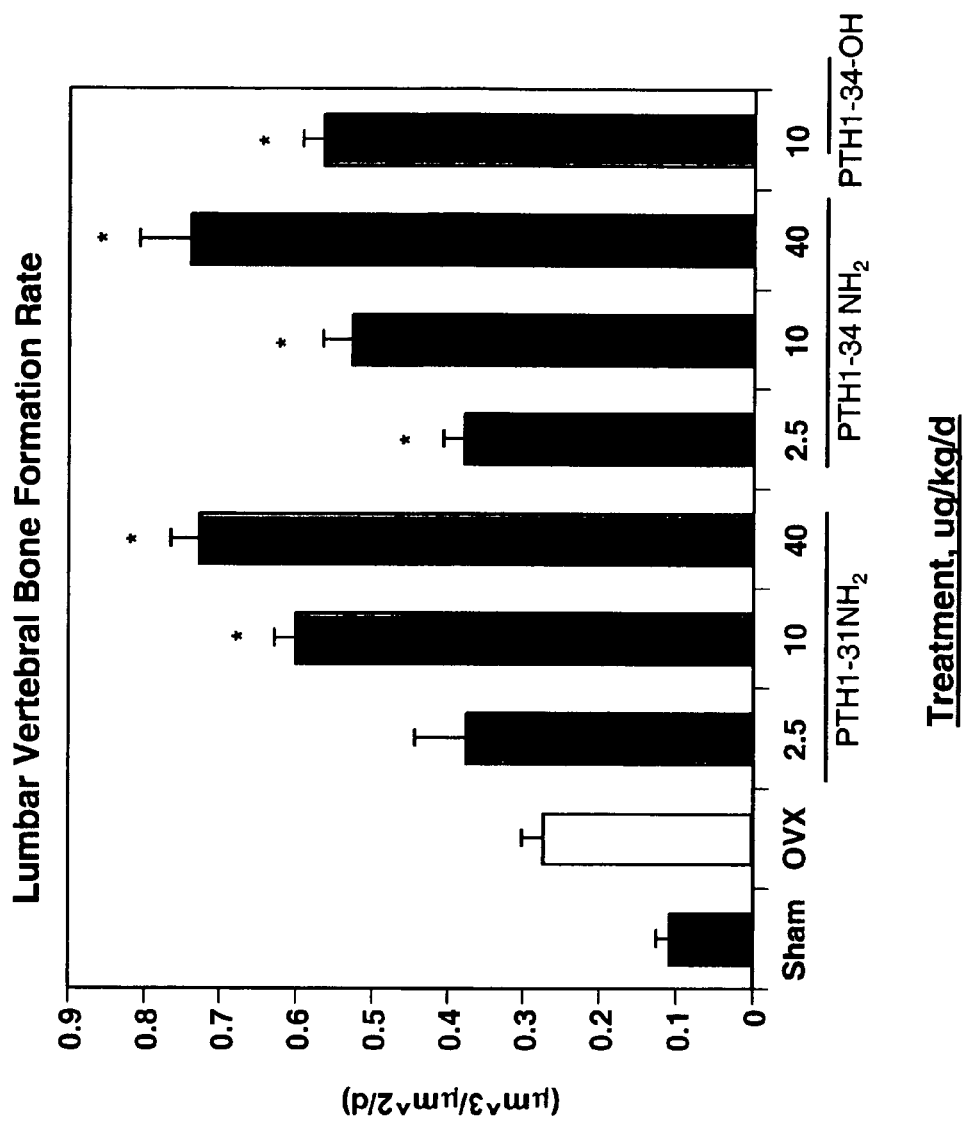

FIG. 9 illustrates the new bone formed in the marrow cavity of groups of rats who underwent the following treatments: control at day 0; control at day 21; sham at day 21; bmx+PBS daily for 7 days; bmx+PBS daily for 14 days; bmx+PBS daily for 21 days; bmx+parathyroid hormone (PTH[1-34]-NH$_2$) daily for 7 days; bmx+parathyroid hormone (PTH[1-34]-NH$_2$) daily for 14 days; bmx+parathyroid hormone (PTH[1-34]-NH$_2$) daily for 21 days; bmx+salmon calcitonin (CT) daily from days 7-14; bmx+CT daily from days 7-21; bmx+parathyroid hormone (PTH[1-34]-NH$_2$) daily from days 1-7 and CT daily from days 7-14; and bmx+parathyroid hormone (PTH[1-34]-NH$_2$) daily from days 1-7 and CT daily from days 7-21. The views in FIG. 9 are at a higher magnification than those in FIG. 8, i.e., for reference, the black bar located in the lower right corner of the figure indicates a measurement of 100 µm;

FIG. 10 (a-b) presents high resolution radiograms of the left and right femurs, respectively, from an additional series of experiments on additional groups of male Sprague-Dawley rats (6 rats per group) aged 9 weeks which were sacrificed and tested after 21 days (3 weeks). The various groups were subjected to the following treatment modalities: Group K—control day 0; Group L—control day 21; Group M—bone marrow ablation (bmx) day 0; Group N—sham day 21; Group O—bmx+phosphate buffer saline (PBS) daily for 21 days; Group P—bmx+PTH[1-34]-NH$_2$ daily for 21 days; Group Q—bmx+parathyroid hormone related peptide (PTHRP) daily for 21 days; and Group R—bmx+rat α-calcitonin gene related peptide (CGRP) daily for 21 days;

FIG. 11 (a-d) are graphical representations of the results of Peripheral Quantitative Computerized Tomography (PQCT) analyses of, respectively, the left (ablated) and right (non-ablated) femoral shafts of the rats from Groups K-R (see description of FIG. 10). FIGS. 11(a) and 11(b) illustrate the trabecular bone density observed in, respectively the left and right femoral shafts at day 21; whereas, FIGS. 11(c) and 11(d) illustrate the total bone density of, respectively, the left and right femoral shafts at the same interval. The meanings of the abbreviations used in FIGS. 11(a-d) are identical to those described above with regard to FIG. 10. The symbols shown in the Figure refer to values that are significantly different. [+=p value<0.01 vs. sham; *=p value<0.01 vs. bmx+PTH; **=p value<0.01 vs. bmx+PTH; and #=p value<0.05 vs. PBS];

FIG. 12 provides a measurement of the serum osteocalcin concentration (in ng/ml) in the blood of the rats in Groups K-R when the rats were sacrificed 21 days after commencement of treatment. The meaning of the abbreviated terms is the same as in FIGS. 10 and 11. Additionally, as in FIG. 11, the asterisks shown in the Figure refer to values that are significantly different from that of the bmx+PBS control. [*=p value<0.05, while **=p value<0.01];

FIG. 13(a-b) illustrate the results of Micro Computerized Tomography (MicroCT) analysis of the left (ablated) and right (non-ablated) femoral shafts of the rats of Groups K-R. The abbreviations are the same as those used in FIGS. 10-12;

FIGS. 14A-14D illustrate a representative series of steps for carrying out a left femur bone marrow ablation in a rat from one of Groups A-J discussed above. FIG. 14A) accessing the distal femur; FIG. 14B) drilling into the bone marrow cavity of the distal femur; FIG. 14C) washing the bone marrow cavity; and FIG. 14D) suturing the incision. Many alternate methods of ablation are possible and thus these figures do not limit the method of the invention;

FIG. 15 is a bar graph comparing the Lumbar Vertebral Bone Mineral Density obtained in osteoporotic female Sprague-Dawley rats wherein the osteoporosis was induced via an ovariectomy. The rats were treated with (1) PTH[1-31]-$NH_2$; (2) PTH[1-34]-$NH_2$; and PTH[1-34]-OH; and FIG. 16 is a bar graph comparing the Lumbar Vertebral Bone Formation Rate obtained in osteoporotic female Sprague-Dawley rats wherein the osteoporosis was induced via an ovariectomy. The rats were treated with (1) PTH[1-31]-$NH_2$; (2) PTH[1-34]-$NH_2$; and PTH[1-34]-OH.

DETAILED DESCRIPTION OF PREFERRED EMBODIMENTS OF THE INVENTION

In a first embodiment the invention provides a method of inducing new bone formation in a subject in need of such inducement. The method comprises the steps of mechanically inducing an increase in osteoblast activity in the subject and elevating blood concentration of at least one bone anabolic agent in the subject. The above steps may be performed in any order, but are to be carried out in sufficient time proximity that the elevated concentration of the anabolic agent and the mechanically induced increase in osteoblast activity at least partially overlap.

Inducement of bone growth may include, for example, generating new or additional bone at locations where such bone growth is not presently taking place and/or stimulating the growth (i.e., increasing the rapidity thereof) of bone which is already in the process of formation. Without being bound in any way by theory, applicants believe that the inducement of bone growth takes place due to the combined effects of (1) a mechanical inducement of osteoblast activity in the subject coupled with (2) an elevation in the blood concentration of at least one bone anabolic agent therein. As used throughout this description, the bone described as being formed by the process of the invention is not limited solely to trabecular bone and should also be taken to include any one or more of the following additional 'types' of bone: compact, cortical and/or lamellar bone.

Mechanical inducement of an increase in osteoblast activity may be obtained, in a preferred embodiment of the invention, by a process of bone marrow irrigation and ablation. Again, without being bound in any way by theory, applicants believe that the bone marrow irrigation and ablation process leads to the formation of a clot within the bone marrow cavity which, through a cascade of biochemical reactions, contributes to increasing osteoblast activity in the subject.

In an another embodiment, the increased osteoblast activity may alternately be obtained by coupling the mechanical inducement with an additional form of inducement such as biochemical inducement. Such biochemical inducement may be obtained by administering to the subject, for example, a quantity of a blood factor such as Factor ("F") VII, Factor VIIa or a combination thereof. Following tissue or vascular injury clotting is initiated by the binding of plasma FVII/FVIIa to tissue factor (tissue thromboplastin). This complex (FVII/FVIIa+Thromboplastin) initiates a sequence of events which leads to activation of the coagulation cascade ultimately leading to fibrin deposition and platelet activation. This complex sequence of events may contribute in part to the stimulation of osteoblasts in the bone marrow. Factors VII and VIIa are commercially available from Novo Nordisk.

The increase in osteoblast activity obtained with the use of the method of the invention may be due to a variety of factors including, but not necessarily limited to (1) osteoblast differentiation, i.e., the production of additional osteoblasts, (2) increasing the activity and/or effectiveness of osteoblasts which are already present in inducing bone formation in the subject, and (3) a combination thereof. In a preferred embodiment of the invention, the increase in osteoblast activity would include all of the above-noted functions.

In one embodiment, the blood concentration of the at least one bone anabolic agent may be elevated by direct administration of one or more bone anabolic agents to the subject.

In a further embodiment of the invention the method additionally comprises "targeting" one or more specific bones of the subject for inducement of bone growth. This targeting is accomplished by mechanically altering the contents of a bone marrow cavity within each targeted bone so as to induce the increased osteoblast activity therein.

The method of the invention is thus useful not only for bone repair, i.e., as in the case of a bone fracture due to trauma, but also for strengthening bone in a site-specific manner in the case of individuals shown by Dual Energy X-Ray Absorptiometry ("DEXA") or other techniques to require an increase in bone mass and/or density to prevent bone fractures, or who suffer due to bone weakness from chronic pain attributable to conditions such as vertebral crush. Moreover, as noted above, the method of the invention additionally serves to provide (and retain) new bone needed to serve as an anchor for prostheses such as artificial hips, knees and shoulders and/or for implants such as dental implants.

In a still further embodiment, the method of the invention additionally comprises providing the subject with an elevated blood concentration of at least one antiresorptive agent, wherein the elevated concentration is sufficient to diminish resorption of new bone growth produced due to the mechanically induced enhanced osteoblast activity according to the invention.

In one embodiment the invention provides a method of inducing bone formation in a subject in need of the same, wherein the method comprises (a) mechanically inducing an increase in osteoblast activity in the subject; and (b) administering to the subject at least one agent that causes elevated blood levels of an endogenous bone anabolic agent within the subject. The method steps may be performed in any order, but in sufficient time proximity that the elevated concentration of the anabolic agent and the mechanically induced increase in osteoblast activity at least partially overlaps. In one embodiment of the method, the agent causing an increased expression of the endogenous bone anabolic agent may be a calcilytic agent. Calcilytic agents useful with the method of the invention include, but are not limited to any agent that limits the binding of calcium to its receptor and thereby triggers the release of endogenous PTH. Examples of such calcilytic compounds are set forth in U.S. Pat. Nos. 6,362,231; 6,395,919; 6,432,656 and 6,521,667, the contents of which are incorporated herein by reference.

The invention additionally provides a method of inducing bone formation in a subject suffering from diminished bone mass or bone trauma. The method includes the step of targeting for treatment at least one bone of the subject, wherein each targeted bone defines a bone marrow cavity therein. The bone marrow cavity contains, inter alia, a quantity of bone marrow and a plurality of osteoblasts. The method of the invention further comprises mechanically altering the contents of the bone marrow cavity to thereby stimulate and thus increase osteoblast activity therein. The method additionally comprises administering to the subject at least one bone anabolic agent for a duration and at a concentration sufficient to raise blood levels of the anabolic agent within the subject above natural levels thereof and thereby prolong the mechanically induced osteoblast activity. For example, a bone anabolic agent endogenously produced in the human body is PTH[1-84] in the free acid form which is naturally found in levels of less than about 8 picomoles (pmoles) per liter in blood of a human subject. Thus the practice of the invention would involve, as indicated above, raising the blood levels of the bone anabolic agent within the subject to levels correspondingly above such natural level. Further to the above, the mechanical alteration of the contents of the bone marrow cavity thus permits specific bones of the subject to be targeted for enhanced bone formation.

In an embodiment of the invention, bone formation may be induced at a location of a long bone fracture in bone of the subject to increase the rapidity of healing of the fracture. In another embodiment, the method further comprises reshaping or modeling at least one targeted bone of a subject by inducing additional bone formation in a controlled manner thereon.

Figure 1:
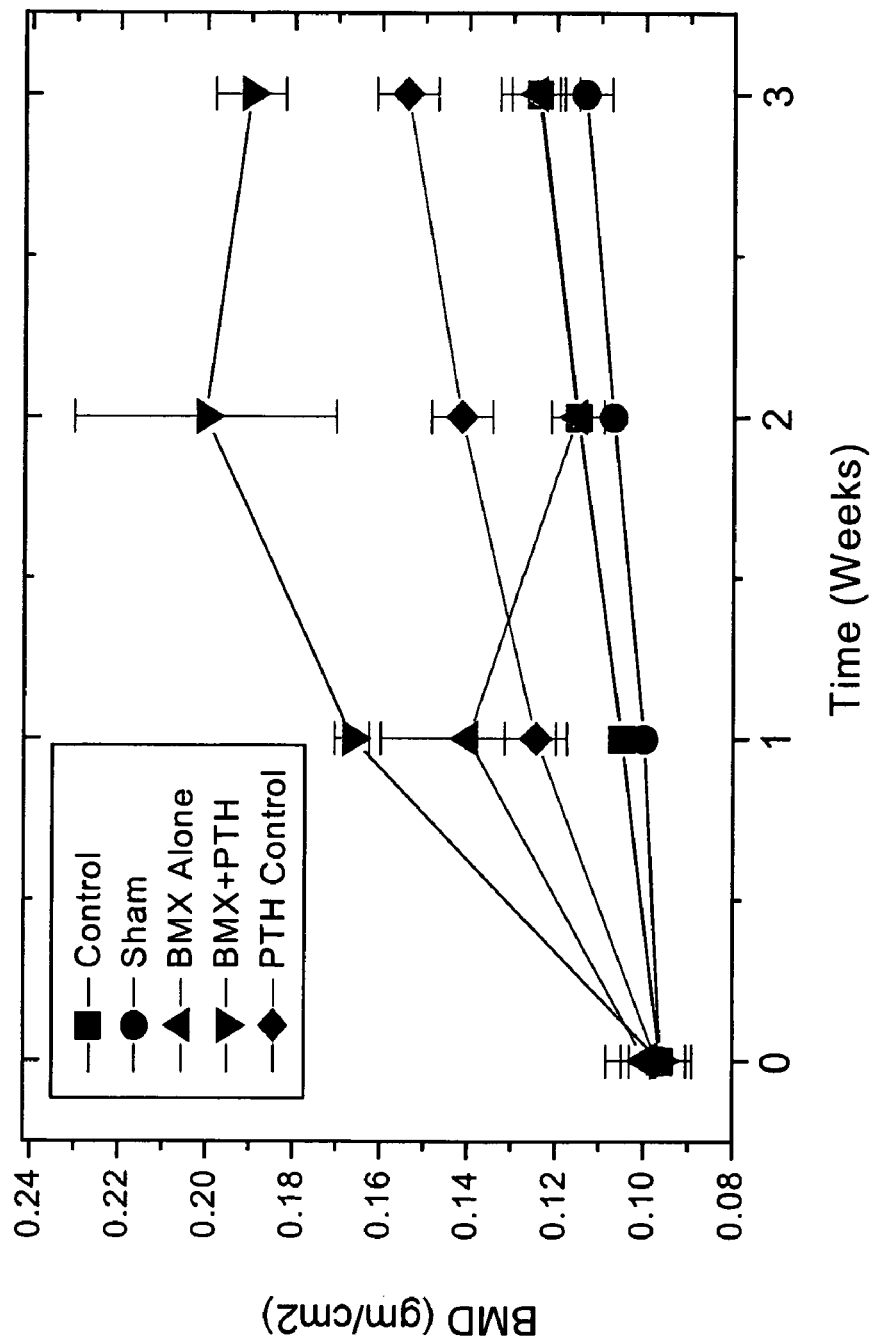

Applicants have surprisingly discovered that an initial burst of osteoblast activity can be sustained at unexpectedly high levels by elevating blood levels of a bone anabolic agent during a time that at least partially overlaps with the initial burst of osteoblast activity. This effect is demonstrated by comparing the curves obtained with Groups C and D in FIG. 1. Absent the bone anabolic agent, the initial burst of bone formation is quickly followed by the resorption of newly formed bone by osteoclasts (see, e.g., the Group C curve in FIG. 1). The curve obtained with Group E of FIG. 1 shows that although increased bone growth is induced due to the administration of a PTH bone anabolic agent alone, this increase does not rise to the level achieved due to the coupling of bone marrow ablation (bmx) plus administration of PTH. The results set forth in FIG. 1 clearly demonstrate that the coupling of bmx and PTH administration provides an unexpected increase in degree, speed and longevity of bone formation relative to the effects of bmx or PTH alone, as well as a targeted site-specific response. Table 1 (below) sets forth the values upon which the curves obtained with Groups A-E in FIG. 1 are based. As no readings were taken for the Control (Group A) and Sham (Group B) groups at Week 1 and Week 2, these values were estimated for purposes of preparing the curves for these two Groups. Table 1, moreover, provides the standard deviations for the values obtained in each Group, which standard deviations are also indicated in FIG. 1.

As indicated herein the bmx treatment was always administered to the rats' left femur and never to the right femur. The non-ablated contralateral femur was analyzed, however, throughout the testing protocols described herein as a control used for detecting the systemic effect of the bone anabolic agent. That is, the results achieved with the contralateral (right) femur permit one to exclude the effect attributable to the bmx treatment. Moreover, analysis of the rats' right femur control also enabled the inventors to determine whether the bmx treatment of the left femur had any effect on other skeletal sites located within the body of the rat.

TABLE 1

| Groups | Femur | BMD (DEXA) (gm/cm$^2$) ± standard deviation | | | |
|---|---|---|---|---|---|
| | | Week 0 | Week 1 | Week 2 | Week 3 |
| Control (Group A) | LEFT | 0.096 ± .007 | 0.105 | 0.115 | 0.124 ± .009 |
| Sham (Group B) | LEFT | 0.096 ± .007 | 0.1 | 0.107 | 0.113 ± .006 |
| BMX ALONE (Group C) | LEFT | 0.099 ± .009 | 0.140 ± .020 | 0.115 ± .006 | 0.124 ± .006 |
| BMX + PTH 1-21 (Group D) | LEFT | 0.096 ± .007 | 0.166 ± .004 | 0.200 ± .030 | 0.190 ± .008 |
| PTH 1-21 (Group E) | RIGHT | 0.097 ± .008 | 0.124 ± .007 | 0.141 ± .007 | 0.154 ± .007 |

As indicated above, the values set forth in FIG. 1 and summarized in Table 1 were obtained with the use of a DEXA technique, which measures the overall density of the entire bone. Peripheral Quantitative Computerized Tomography ("pQCT") however, provides the density of a virtual "slice" of the bone at any selected site. pQCT values obtained by the inventors were obtained at the epipyhis level of the bone, which is the site where the bone was drilled, and hence destroyed. Thus, the pQCT measurements taken by the inventors during the above-discussed experiments did not demonstrate an improvement in total bone content for the combination of bmx+PTH relative to PTH alone. This is due to the fact that the bmx surgery consisted in drilling through the epiphyseal bone (both the cortical and trabecular portions), which destroys the bone and thus caused the pQCT to read a negative bone density.

Figure 2:
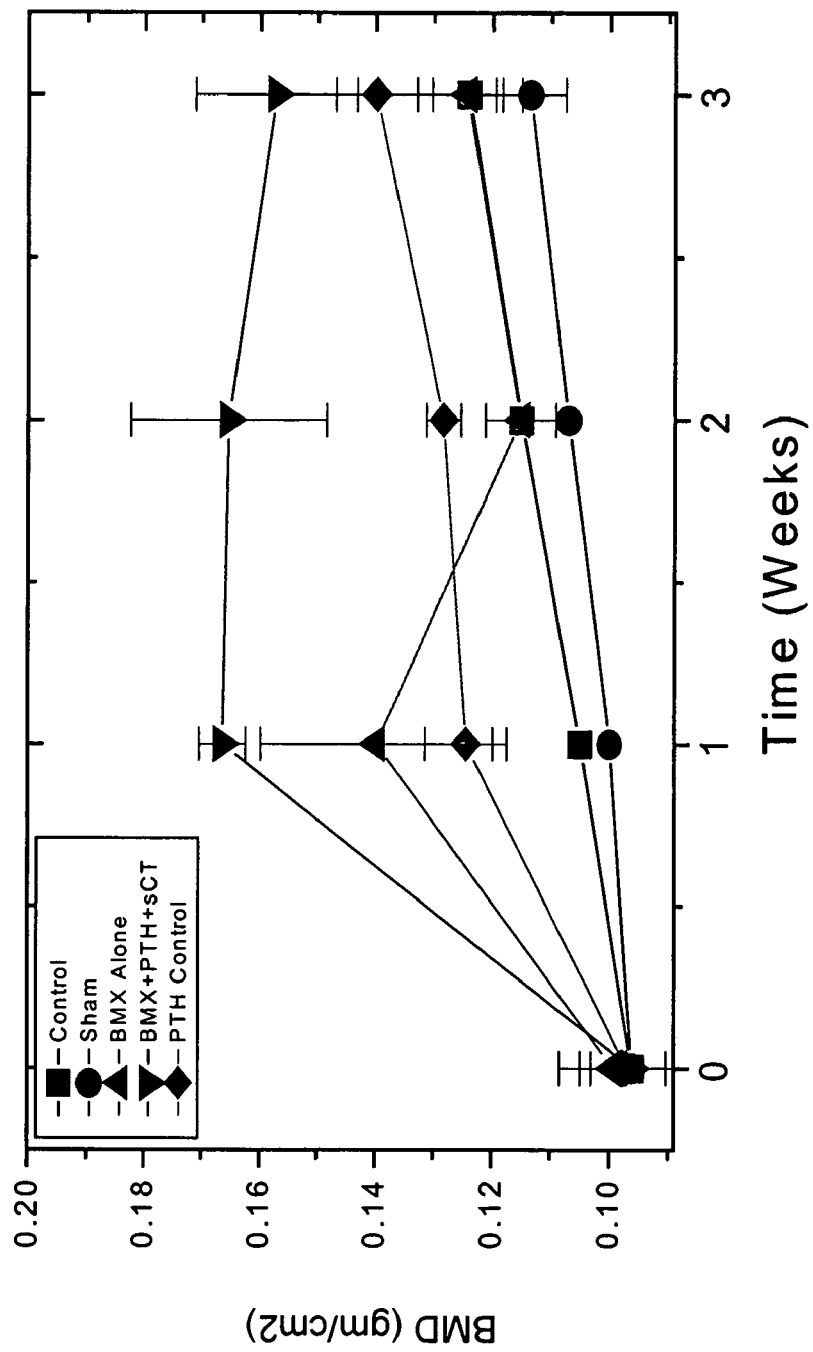

FIG. 2 is provided to illustrate, inter alia, the further beneficial effect achieved due to the overlapping (i.e., with PTH administration) or subsequent administration of the antiresorptive agent salmon calcitonin (sCT). First, a comparison of the curves obtained with Group H (bmx alone) and Group J (PTH+sCT with no bmx) to that obtained with Group I (bmx+PTH+sCT) provide still further evidence of the synergistic effect attributable to the use of the method of the invention. Additionally, the curve obtained with Group I also demonstrates that the administration of the antiresorptive agent sCT following the initial burst of osteoblast activity which occurs due the coupling of bmx and PTH administration, significantly diminishes the proportion of the newly formed bone which is resorbed due to the action of the osteoclasts. Table 2 (below) sets forth the values upon which the curves of FIG. 2 are based. As no readings were taken for the Control (Group F) and Sham (Group G) during Weeks 1 and 2, these values were estimated for purposes of preparing the curves. Table 2 provides the standard deviations for the values obtained in each Group, which standard deviations are also indicated in FIG. 2.

TABLE 2

| Groups | Femur | BMD (DEXA) (gm/cm$^2$) ± standard deviation | | | |
|---|---|---|---|---|---|
| | | Week 0 | Week 1 | Week 2 | Week 3 |
| Control (Group F)* | LEFT | 0.096 ± .007 | 0.105 | 0.115 | 0.124 ± .009 |
| Sham (Group G)* | LEFT | 0.096 ± .007 | 0.1 | 0.107 | 0.113 ± .006 |
| BMX ALONE (Group H)* | LEFT | 0.099 ± .009 | 0.140 ± .020 | 0.115 ± .006 | 0.124 ± .006 |
| BMX + PTH 1-7 + sCT 7-21 (Group I) | LEFT | 0.096 ± .007 | 0.166 ± .004 | 0.165 ± .017 | 0.157 ± .014 |
| PTH 1-7 + sCT 7-21 (Group J) | RIGHT | 0.097 ± .008 | 0.124 ± .007 | 0.128 ± .003 | 0.140 ± .007 |

*Groups F, G and H are the same as Groups A, B and C (see Table 1).

Figure 3:
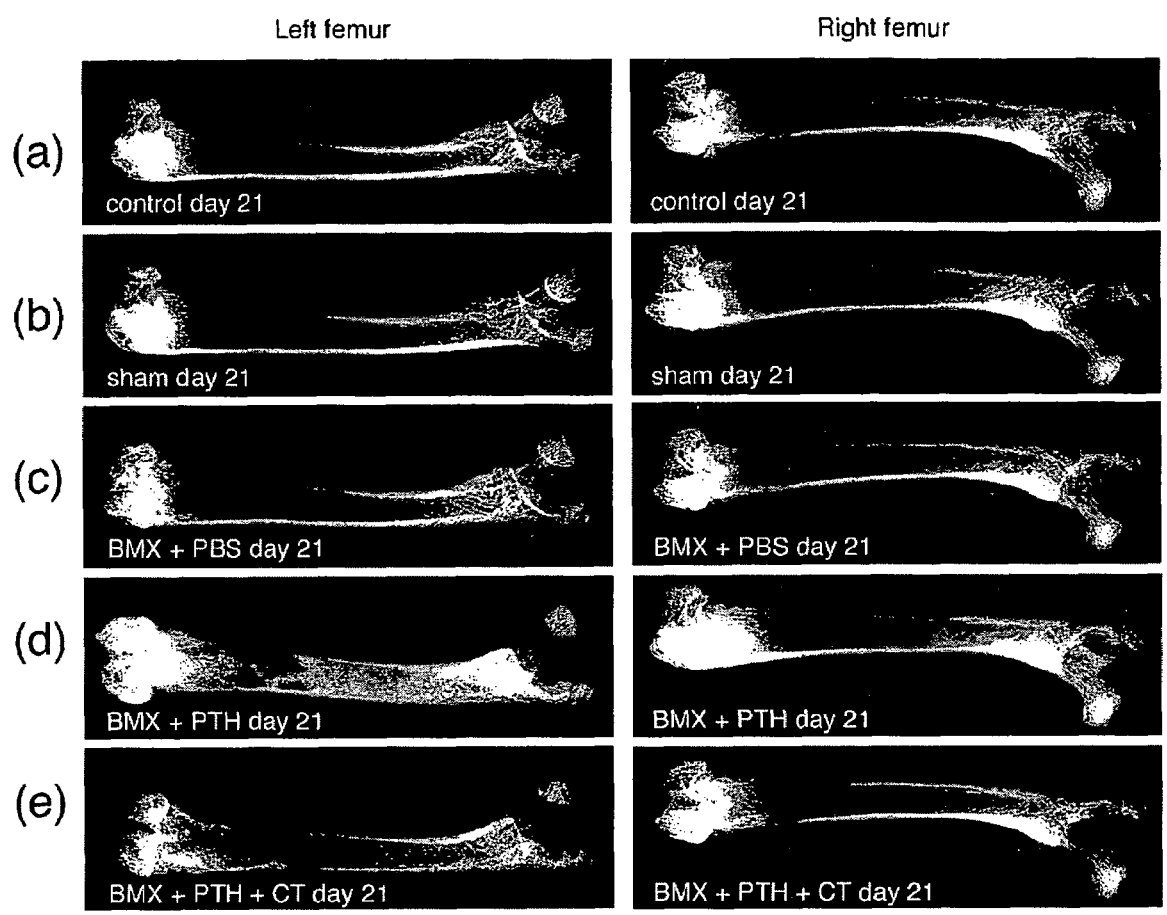

FIG. 3 presents a set of high resolution radiograms of the entire left and right femurs from rats taken from some of the groups A-J described above. In each of the views shown, the treatment modality is indicated in the lower left corner of the radiogram. The following abbreviations are used: Control=no surgery; Sham=surgery without any bone marrow ablation; BMX=bone marrow ablation; PBS=phosphate buffer saline; PTH=parathyroid hormone (PTH[1-34]-NH$_2$); and CT=salmon calcitonin. Furthermore, as indicated above, in those right femur views in FIGS. 3(c)-(e), which indicate "bmx" in the description of the treatment modality, this refers to the fact that the corresponding, i.e., left, femur to that shown was subjected to the bmx treatment. This usage, moreover, remains consistent throughout the remainder of this discussion. The lighter (more radio-opaque) areas appearing in the radiograms indicate areas of more dense bone growth.

As shown in the Figure, the best results, i.e, greatest bone growth, were achieved with the use of the bone marrow ablation (bmx) technique, coupled with the administration of an anabolic agent, such as parathyroid hormone, with or without the presence of an anti-resorptive agent such as salmon calcitonin. See, particularly, FIGS. 3(d) and 3(e). Although there was improvement in the right (non ablated) femur attributable to the administration of the anabolic agent (i.e, PTH daily for 21 days in the case of FIG. 3(d) and PTH daily for days 1-7, followed by daily administration of salmon calcitonin for days 7-21 (FIG. 3e), the corresponding left femur showed even greater improvement than the right, due to the combined effects of the application of the bmx treatment and the administration of the anabolic agent All of the data presented above are based on analyses carried out solely of the distal epiphysis portion of the rat femurs. Subsequently, however, to avoid the above-described drawbacks associated with reading the bone density at the level of the epiphysis, the inventors undertook to further analyze the remaining portions of the animals' femur bones and particularly, areas along the length of the cortical shaft. The midshaft portion of the bone was chosen because, in contrast to measurements taken at the epiphysis portion of the bone, it is relatively simple at this alternate location to measure the increase in trabecular bone formed within the shaft marrow cavity because the bone marrow cavity normally does not contain trabecular bone, only bone marrow cells, unless and until the bone is treated by the method of the present invention, as described herein. In the discussion which follows, directed to the results of these additional analyses, the reader is reminded that the bone marrow ablation (bmx) technique was practiced, in all cases, only on the left femur of the test animals. That is to say, there was no ablation of the marrow portion in the right femur. Thus, in the right femur views discussed below, wherein the illustration or graph relating to the right femur is labeled with the abbreviation "bmx", etc. to describe the modality of treatment which the rat was subjected to, one should understand such labeling to mean that the view is of a right femur, or is of a graph which presents a value obtained pursuant to the analysis of such right femur, wherein the animal's corresponding left femur underwent a bone marrow ablation treatment in the manner described herein. The results of the analyses noted herein and described further below clearly demonstrate an improvement in total bone content for the combination of bmx+PTH relative to PTH alone, which improvement was present, but simply not detectable, in the pQCT analysis of the bone.

Figure 4:
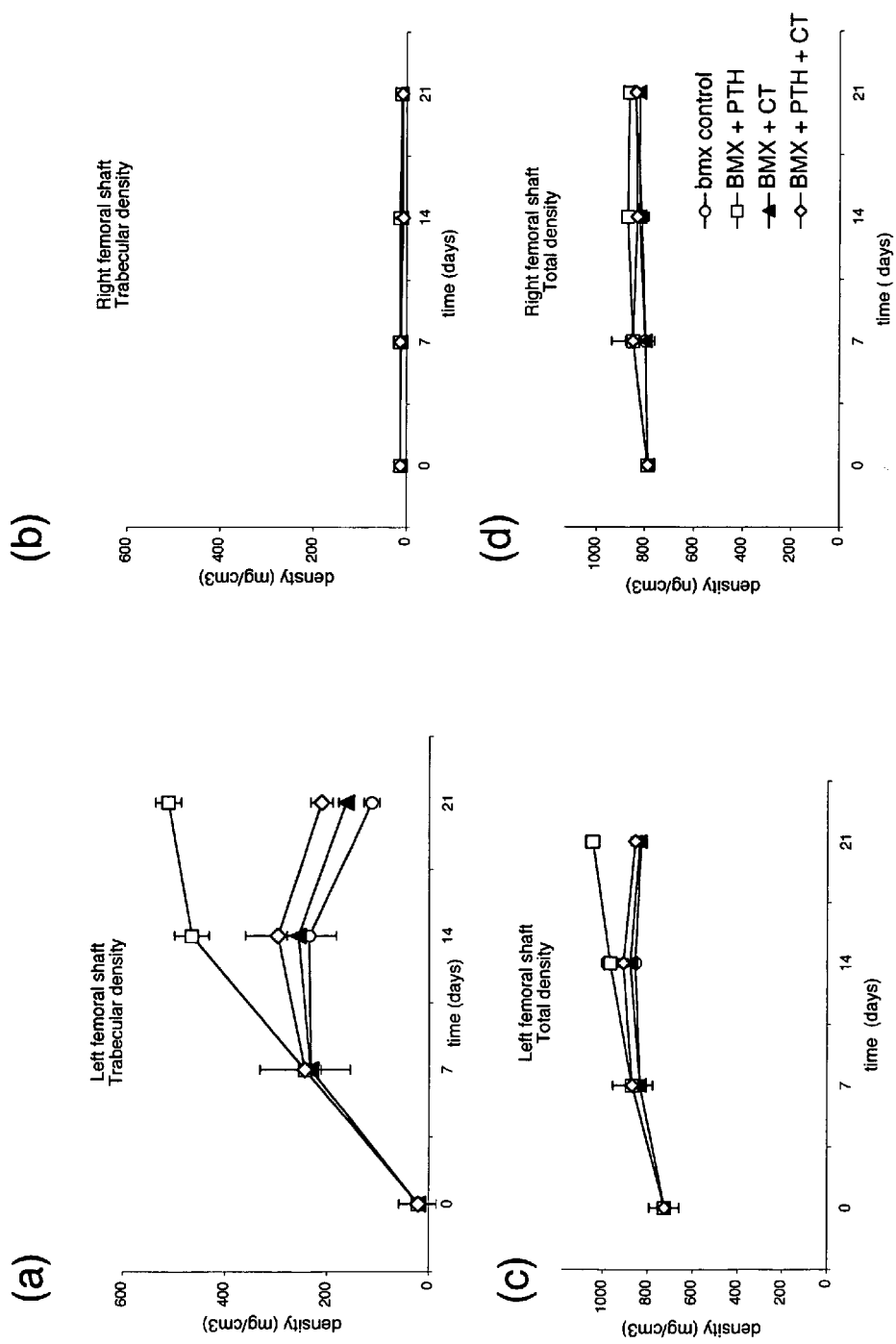

FIGS. 4 (a-d) graphically illustrate the formation of both trabecular bone and, to some extent, total bone, within the left femoral shaft in rats from the Groups described in Tables 1 and/or 2 above, wherein the left femur was subjected to a bmx (bone marrow ablation) treatment coupled with a concurrent and/or subsequent administration of one or more bone anabolic agents, including parathyroid hormone (PTH[1-34]-NH$_2$) and one or more anti-resorptive agents such as salmon calcitonin. As may be seen from the figures, the greatest formation of new trabecular bone occurred in the left femoral shaft due to the combined effect of bmx with parathyroid hormone. The next highest level of new bone formation occurred due to the administration of parathyroid hormone for 7 days, followed by a subsequent administration of salmon calcitonin. Beneficial results were additionally observed with the combination of bmx plus salmon calcitonin. The effects of these last two combinations protects the significant initial bone formation induced by bmx, but not to the same extent as parathyroid hormone (PTH[1-34]-NH$_2$) alone. The least effective combination, i.e., in improving bone density, the effect of which also diminished most rapidly over time, was bmx+a buffer (phosphate buffer saline or "PBS") wherein the buffer, taken by itself, has no known anabolic effect.

FIGS. 4(b) and 4(d) are provided to illustrate the results obtained with the same animals' corresponding right femoral shafts, i.e, in which bone marrow ablation (bmx) was not performed. Little or no new bone formation was observed, i.e, the density remained substantially constant, since the only treatment received by the right femurs was due to the systemic administration of the bone anabolic agent. The agent(s) was administered for too short a period to have, by itself, any real positive effect on the bone density. In fact, the total bone density curve for the right femoral shaft presents a substantially straight line, which is attributable to the fact that the total density measurement includes a measurement of cortical bone. Furthermore, since the anabolic agent was not administered for a period sufficient to increase cortical bone density, the total density remained unchanged.

Table 3 (below) sets forth the values upon which the curves of FIGS. 4 (a-d) are based. The table additionally includes the standard deviations ("sd") for the values obtained for each analysis, which standard deviations are also indicated in FIGS. 4 (*a-d*).

TABLE 3

| Groups | Day | | | | | | | |
|---|---|---|---|---|---|---|---|---|
| | 0 | | 7 | | 14 | | 21 days | |
| | mean | sd | mean | sd | mean | sd | mean | sd |
| Left femoral shaft Trabecular density (mg/cm³) | | | | | | | | |
| bmx control (Group C/H) | 21.4 | 37.1 | 232.2 | 20 | 235.1 | 52.4 | 113.3 | 15.4 |
| BMX + PTH (Group D) | 21.4 | 37.1 | 243.8 | 88.1 | 465.4 | 33.4 | 511.2 | 25 |
| BMX + CT | 21.4 | 37.1 | 232.2 | 20 | 257 | 21.4 | 163.5 | 15 |
| BMX + PTH + CT (Group I) | 21.4 | 37.1 | 243.8 | 88.1 | 296.1 | 63.9 | 211.2 | 21.6 |
| Left femoral shaft Total density (mg/cm³) | | | | | | | | |
| bmx control (Group C/H) | 726.1 | 67.1 | 833.6 | 16.8 | 853.8 | 28 | 830.1 | 32.6 |
| BMX + PTH (Group D) | 726.1 | 67.1 | 867.5 | 27.2 | 968.7 | 36 | 1046.7 | 26 |
| BMX + CT | 726.1 | 67.1 | 833.6 | 16.8 | 876.2 | 30.4 | 833.2 | 30 |
| BMX + PTH + CT (Group I) | 726.1 | 67.1 | 867.5 | 88.1 | 908.1 | 20.4 | 855 | 18.7 |
| Right femoral shaft Trabecular density (mg/cm³) | | | | | | | | |
| bmx control (Group C/H) | 12.9 | 21.6 | 1.2 | 1.3 | 12.3 | 1.7 | 8.8 | 3.5 |
| BMX + PTH (Group D) | 12.9 | 21.6 | 1.5 | 9 | 13.7 | 2.4 | 10.7 | 2.6 |
| BMX + CT | 12.9 | 21.6 | 1.2 | 1.8 | 10.9 | 3 | 10.8 | 2.1 |
| BMX + PTH + CT (Group I) | 12.9 | 21.6 | 1.5 | 9.1 | 7.5 | 6.4 | 8.7 | 2.5 |
| Right femoral shaft Total density (mg/cm³) | | | | | | | | |
| bmx control (Group C/H) | 787.2 | 19.1 | 797.4 | 13.2 | 811 | 26.1 | 840 | 12.8 |
| BMX + PTH (Group D) | 787.2 | 19.1 | 848.2 | 32.6 | 871 | 25 | 864.8 | 25.4 |
| BMX + CT | 787.2 | 19.1 | 797.4 | 16.8 | 821.9 | 31.5 | 821.3 | 19.6 |
| BMX + PTH + CT (Group I) | 787.2 | 19.1 | 848.2 | 88.1 | 830.5 | 21.6 | 836.7 | 16.3 |

Figure 5:
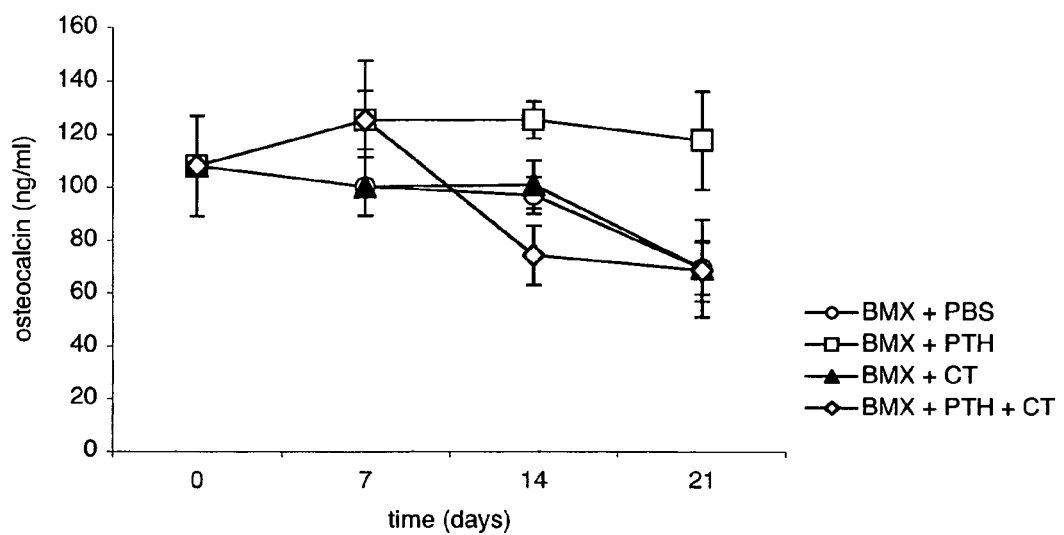

FIG. 5 provides a graphical representation of the osteocalcin levels determined, at the time of sacrifice, in the serum of rats subjected to the following treatment modalities: bmx+ PBS; bmx+parathyroid hormone (PTH[1-34]-NH$_2$); bmx+ salmon calcitonin (CT); and bmx+parathyroid hormone (PTH[1-34]-NH$_2$)+CT. It is well known by those of ordinary skill in this art that osteocalcin is a biochemical marker related to the number of osteoblasts, i.e, a measure of new bone growth, which may be measured in the blood serum of the animal. In FIG. 5, the highest and most consistent level of osteocalcin was found in the serum of animals who underwent bone marrow ablation (bmx) plus treatment with parathyroid hormone (PTH[1-34]-NH$_2$). PTH treatment increased osteocalcin levels in as early as 7 days and the higher levels persisted up to 21 days. Moreover, the combination of bmx+salmon calcitonin provided a relatively steady state value of osteocalcin for at least two weeks (14 days). This was completely expected since CT is an anti-resorptive agent and thus its administration reduces the number of osteoclasts but does not increase the number of osteoblasts. That is, administering CT reduces the rate of bone turn-over.

Table 4 (below) sets forth the values upon which the curves of FIG. 5 are based. Table 4 additionally provides the standard deviations for the values obtained during each of the indicated analyses, which standard deviations are also indicated in FIG. 5.

TABLE 4

| | Osteocalcin (ng/ml) | | | | | | | |
|---|---|---|---|---|---|---|---|---|
| | Day | | | | | | | |
| | 0 | | 7 | | 14 | | 21 days | |
| Groups | mean | sd | mean | sd | mean | sd | mean | sd |
| bmx control (Group C/H) | 108.2 | 19.1 | 100.5 | 11 | 97 | 6.9 | 69.5 | 18.5 |
| BMX + PTH (Group D) | 108.2 | 19.1 | 125.5 | 22.3 | 125.4 | 10.7 | 117.8 | 15 |
| BMX + CT | 108.2 | 19.1 | 100.5 | 11 | 101 | 9 | 69.5 | 10 |
| BMX + PTH + CT (Group I) | 108.2 | 19.1 | 125.5 | 22.3 | 74.3 | 11.4 | 68.6 | 11.6 |

Figure 6:
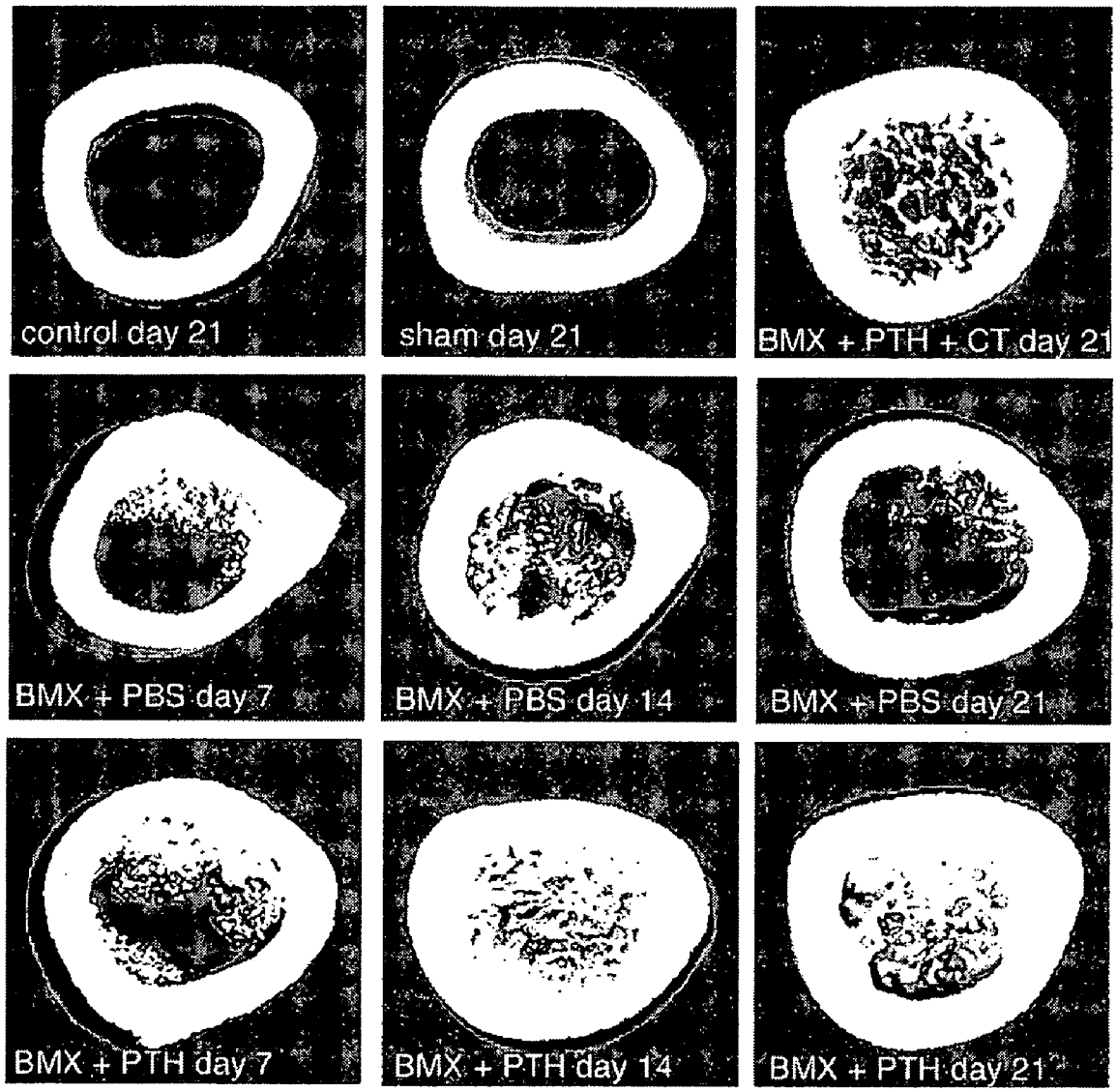
FIG. 6 illustrates the results of Micro Computerized Tomography (MicroCT) analyses of the left (ablated) femoral shafts of the rats which are the subjects of FIGS. 3-4. The abbreviations mean the same as in FIGS. 3-5.

FIG. 6 illustrates the results of a Micro Computerized Tomography (MicroCT) analysis of representative bones taken from the left femoral shaft of control and treated rats. The modality of treatment is set forth in the lower left corner of each of the views, and the abbreviations used therein are the same as those which appear in FIGS. 3-5. The Figure provides a view through a section of each such bone shaft. As can be seen, the best results, i.e, the most extensive new bone growth, was achieved in the case of bone marrow ablation (bmx)+parathyroid hormone (PTH[1-34]-NH$_2$) daily for 7 days; bmx+parathyroid hormone daily for 14 days; bmx+ parathyroid hormone daily for 21 days; and bmx+parathyroid hormone during days 1-7, followed by the administration of salmon calcitonin during days 7-21. As expected, no new bone growth was observed in both the control and the sham and only transient new bone growth was achieved in the case of treatment with bmx and the PBS buffer solution.

Figure 7:
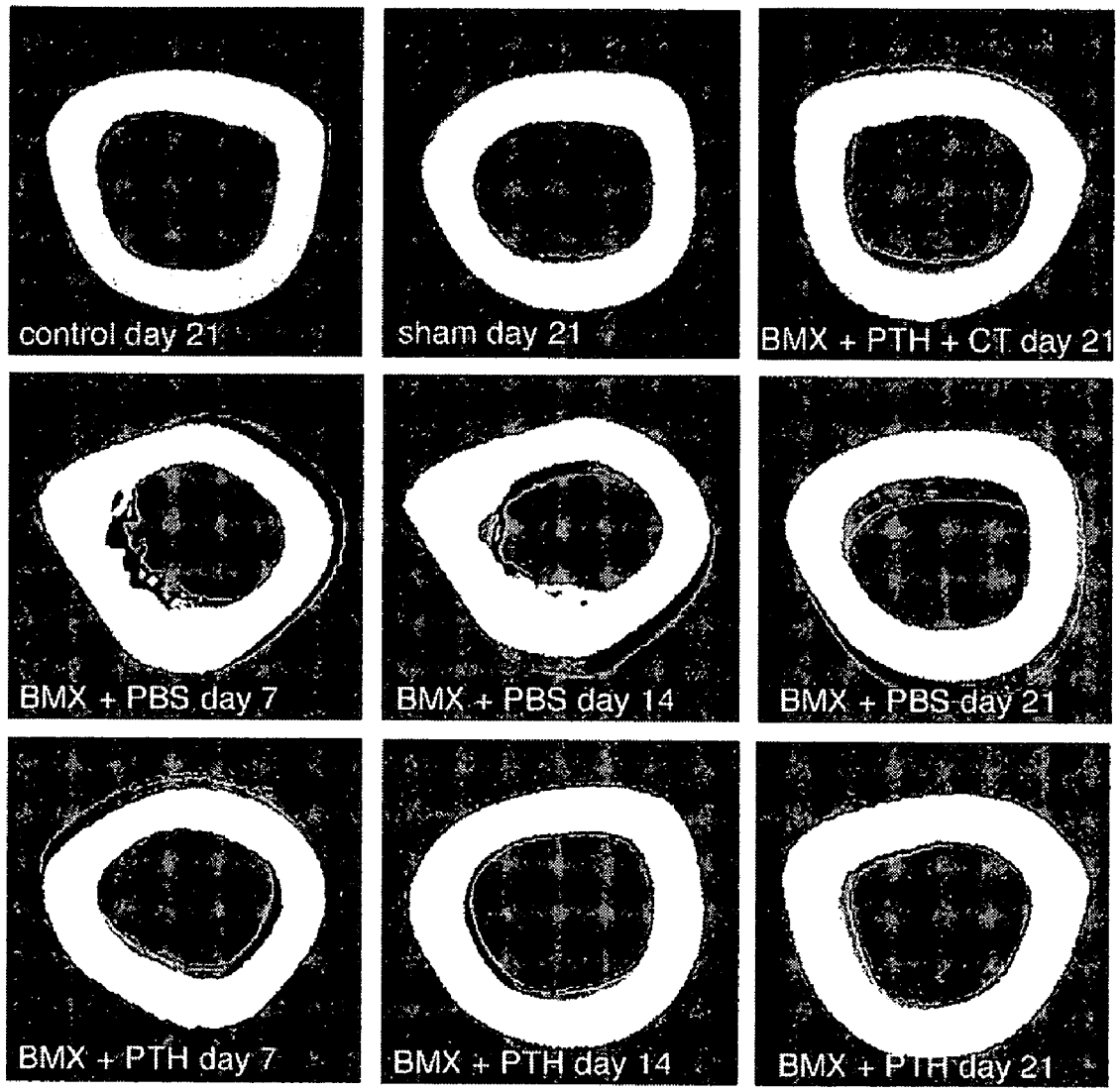
FIG. 7 is similar to FIG. 6 but illustrates the results of a Micro Computerized Tomography (MicroCT) analysis of the right (non-ablated) femoral shafts of the same rats. The abbreviations stand for the same treatments as in FIGS. 3-7.

FIG. 7 provides the results of MicroCT analysis on femoral sections obtained from the right femoral shaft of the same rats tested as in FIG. 6. As may be seen in the figure, there was substantially no additional newly formed bone within the interior marrow cavity of the bone shaft. This is due to the fact that the right femur did not undergo ablation treatment. Again, it is to be noted that any right femur view labeled with "bmx" should be taken to mean that it was the corresponding left femur which underwent bone marrow ablation. Any additional growth occurring within the right femoral shaft, therefore, is attributable to the systemic effect of the anabolic agent administered to the animal in question.

FIG. 8 provides views of stained and decalcified bone sections of the left femur of representative rats subjected to the following treatment modalities: Control day 0; Control day 21; Sham day 21; bmx day 0; bmx+PBS daily for 7 days; bmx+PBS daily for 14 days; bmx+PBS daily for 21 days; bmx+parathyroid hormone (PTH[1-34]NH$_2$) daily for 7 days; bmx+PTH daily for 14 days, and bmx+PTH daily for 21 days. As demonstrated by the Figure, there is an obvious improvement, i.e, increase, in bone growth within the marrow cavity of femurs from rats subjected to the concurrent effects of a bone marrow ablation+administration of an anabolic agent. Moreover, the greatest such increase is seen in the case where the bmx treatment is coupled with the longest administration of the anabolic agent, that is, in the case of bmx+PTH daily for 21 days. These views provide substantial additional evidence of the efficacy of the method of the present invention.

FIG. 9 is a view, taken at a higher magnification than the views in FIG. 8, within the left femoral bone marrow cavity of rats subjected to the following treatment modalities: a) control day 0, b) control day 21, c) sham day 21, d) bone marrow ablation (bmx)+phosphate buffer saline (PBS) daily for 7 days, e) bmx+PBS daily for 14 days, f) bmx+PBS daily for 21 days, g) bmx+parathyroid hormone (PTH[1-34]NH$_2$) daily for 7 days, h) bmx+PTH daily for 14 days, i) bmx+PTH daily for 21 days, j) bmx+salmon calcitonin (CT) daily from days 7-14, k) bmx+salmon calcitonin daily for days 7-21, l) bmx+PTH daily for days 1-7, followed by salmon calcitonin daily during days 7-14, and m) bmx+PTH daily for days 1-7, followed by salmon calcitonin daily during days 7-21. This figure provides additional evidence in support of the efficacy of the method of the invention in rapidly forming new bone where needed. As can be seen from the figure, in all instances wherein the bone marrow cavity was subjected to ablation ("bmx") and the effect of this procedure was overlapped with the bone-producing effects of anabolic agents such as parathyroid hormone (PTH[1-34]-NH$_2$) and/or salmon calcitonin, a significant amount of new bone growth was achieved and the density of the new bone increased with time. In addition, this figure shows that the newly formed bone became denser and more regular with time, and hence, of greater mechanical strength.

An additional series of experiments was thereafter carried out with additional groups of rats (K-R) in order to (1) measure the effect of additional bone anabolic agents, i.e., other than parathyroid hormone (PTH[1-34]-NH$_2$) and calcitonin, as well as to compare the effect(s) achieved with such parathyroid hormone with those obtained with the use of alternate anabolic agents, including parathyroid hormone related peptide (PTHrP) and calcitonin gene related peptide (CGRP). As in the case of the analyses discussed above with regard to FIGS. 3-9, in the animals tested only the left femur underwent the bone marrow ablation (bmx) procedure, i.e., there was no ablation of the right femur. Thus, as noted above, any views of the right femur in the figures described below indicating bone marrow ablation (bmx) as a treatment modality should be taken to mean that such treatment was applied to the corresponding left femur. Further, as was additionally the case above, the samples described below with regard to FIGS. 10-13 were taken from the femur shafts, rather than the corresponding distal epiphysis as in the case of FIGS. 1 and 2. The figures discussed below depict the results of end-point studies wherein the measurements were taken only at the 21 day end-point.

FIG. 10 (a-b) presents a set of high resolution radiograms of the entire left and right femurs of additional (to those described above) groups of rats, injected daily for a designated term with one or more of the following agents: phosphate buffer saline (PBS); parathyroid hormone (PTH[1-34]-NH$_2$); parathyroid hormone related peptide (PTHrP); and calcitonin gene related peptide (CGRP). The rats chosen for test subjects were subjected to the following treatment modalities (as indicated in the lower left corner of each of the radiograms): control day 0; control day 21; bone marrow ablation (bmx) day 0; sham day 21; bmx followed by injection of PBS buffer daily for 21 days; bmx followed by injection of PTH daily for 21 days; bmx followed by injection of PTHrP daily for 21 days; and bmx followed by injection of CGRP daily for 21 days.

As shown by FIG. 10(a), the best results, i.e., the greatest bone density, was obtained in the left femur wherein the effect of the bone marrow ablation overlapped with that attributable to the administration of the various anabolic agents. As in the case of FIG. 3, the lighter, i.e, more radio-opaque, areas indicate the locations of the greatest additional bone growth. The best results were once again obtained with the use of the parathyroid hormone as the anabolic agent, but satisfactory results were also returned with the use of, respectively, PTHrP and CGRP as the anabolic agent. Once again, as also indicated in FIG. 3, the left femur showed a correspondingly greater improvement than did the right, which is again attributable to the bmx treatment accorded the left femur, in contrast to the right femur which underwent no such treatment.

FIG. 11 (a-d) graphically illustrates, by means of a bar graph, the improvements in trabecular bone density and, to some extent, total bone density, in the left femoral shaft of rats subjected to the treatment modalities described above with regard to FIG. 10 (a-b); that is, control day 0; bmx day 0; control day 21; sham day 21; bmx+PBS on day 21; bmx+PTH on day 21; bmx+PTHrP on day 21; and bmx+CGRP on day 21. Again, this is attributable that (only) the left femur was subjected to the bmx treatment, and thus was the only femur wherein the effects of such bmx treatment overlapped with that of the systemic treatment with the bone anabolic agent. As can be clearly discerned from, for example, FIG. 11(a) the trabecular bone density of the animals' left femoral shaft was significantly improved following bone marrow ablation, in conjunction with which the animals were treated with, respectively, parathyroid hormone, PTHrP and CGRP. FIG. 11(c) also shows some increase in total bone density as determined in the left femoral shaft following bmx treatment linked with anabolic agent administration. In contrast to the values obtained for the left femur, no significant amount of bone was formed in the right femur, notwithstanding whether it is trabecular bone density or total bone density which is being measured. This lack of new bone is, furthermore, attributable to the fact that the right femur had not been subjected to the bone marrow ablation (bmx) treatment.

Table 5 (below) sets forth the values upon which the height of the bars in FIGS. 11 (a-d) are based. The table additionally includes the standard deviations for the values obtained for each analysis, which standard deviations are also indicated in FIGS. 11 (a-d).

TABLE 5

|  | mean | sd |
|---|---|---|
| Left femoral shaft Trabecular density (mg/cm$^3$) | | |
| control day 0 (Group K) | 140 | 12.9 |
| BMX day 0 (Group M) | 122.1 | 16.9 |
| control day 21 (Group L) | 106.4 | 6.8 |
| sham day 21 (Group N) | 108.9 | 7.8 |
| BMX + PBS day 21 (Group O) | 254.7 | 54.4 |
| BMX + PTH day 21 (Group P) | 540.7 | 40.7 |
| BMX + PTHRP day 21 (Group Q) | 403.1 | 64.3 |
| BMX + CGRP day 21 (Group R) | 283.5 | 47.5 |
| Left femoral shaft Total density (mg/cm$^3$) | | |
| control day 0 (Group K) | 858.3 | 12.8 |
| BMX day 0 (Group M) | 852.3 | 9.1 |
| control day 21 (Group L) | 826.7 | 21.2 |
| sham day 21 (Group N) | 842.6 | 25.1 |
| BMX + PBS day 21 (Group O) | 923.6 | 34.5 |
| BMX + PTH day 21 (Group P) | 1100.2 | 18.3 |
| BMX + PTHRP day 21 (Group Q) | 1017.9 | 30.9 |
| BMX + CGRP day 21 (Group R) | 963.5 | 30.5 |

TABLE 5-continued

|  | mean | sd |
|---|---|---|
| Right femoral shaft Trabecular density (mg/cm$^3$) | | |
| control day 0 (Group K) | 133.5 | 13.3 |
| BMX day 0 (Group M) | 132.8 | 10.5 |
| control day 21 (Group L) | 113.5 | 6.7 |
| sham day 21 (Group N) | 111.3 | 6.3 |
| BMX + PBS day 21 (Group O) | 111.8 | 6.9 |
| BMX + PTH day 21 (Group P) | 128.3 | 4.8 |
| BMX + PTHRP day 21 (Group Q) | 122.4 | 11.9 |
| BMX + CGRP day 21 (Group R) | 115.5 | 9.1 |
| Right femoral shaft Total density (mg/cm$^3$) | | |
| control day 0 (Group K) | 855.2 | 13.9 |
| BMX day 0 (Group M) | 863.1 | 20.9 |
| control day 21 (Group L) | 833.8 | 11.4 |
| sham day 21 (Group N) | 848.6 | 27.1 |
| BMX + PBS day 21 (Group O) | 836.2 | 34 |
| BMX + PTH day 21 (Group P) | 899.5 | 24 |
| BMX + PTHRP day 21 (Group Q) | 858.2 | 22.2 |
| BMX + CGRP day 21 (Group R) | 831.1 | 31.8 |

FIG. 12 is a bar graph which sets forth the osteocalcin levels determined, at the time of sacrifice, in the blood serum of the rats which were the subject of the analyses illustrated in FIGS. 10 and 11. As indicated above, it is well known that osteocalcin is a biochemical marker indicative of new bone growth. As can be seen in FIG. 12, the highest osteocalcin level, i.e, indicating the greatest bone growth, occurs due to the combination of bmx+the administration of parathyroid hormone (PTH[1-34]-NH$_2$) on a daily basis for 21 days. Significant new bone growth is also shown with the combination of bmx+PTHrP administered daily for 21 days Although the treatment with CGRP showed a trend toward increase in trabecular bone density (see, e.g, FIG. 11 and Table 5), there is no increase seen in osteocalcin levels with CGRP treatment. This probably indicates that the anabolic activity of CGRP is weaker than that of PTH or PTHrP and hence, longer periods of treatment or higher concentrations of CGRP may be required to provide a measurable increase in osteocalcin levels.

Table 6 (below) sets forth the values upon which the height of the bars in FIG. 12 are based. The table additionally includes the standard deviations for the values obtained for each analysis, which standard deviations are also included in FIG. 12.

TABLE 6

| Osteocalcin (ng/ml) | | |
|---|---|---|
|  | mean | sd |
| control day 0 (Group K) | 120.6 | 5.2 |
| control day 21 (Group L) | 109 | 7.7 |
| sham day 21 (Group N) | 100 | 11.4 |
| BMX + PBS day 21 (Group O) | 102.8 | 15 |
| BMX + PTH day 21 (Group P) | 141.5 | 15.4 |
| BMX + PTHRP day 21 (Group Q) | 124.2 | 11.2 |
| BMX + CGRP day 21 (Group R) | 97 | 11.3 |

FIG. 13 (a-b) provides a comparison between Micro Computerized Tomography (MicroCT) analyses of bone samples taken from the left femoral shaft (FIG. 13a) and the right femoral shaft (FIG. 13b) of rats treated in the manner indicated in FIGS. 10-12. As in the other cases discussed above, the most significant amount of new bone growth is found in the shaft of the left femur, since this shaft was subjected to the bmx treatment. In particular, a significant degree of improvement is noted in rats treated with (a) bmx+PTH administered for 21 days, and (b) bmx+PTHrP administered for 21 days, while new bone growth, although lesser in scope than in the case of (a) and (b) above, was noted for the combination of bmx+CGRP. In contrast, the right femoral shaft sections show very little or no increase in bone growth at all.

The results set forth in FIGS. 1, 2, 4, 5, 11 and 12 and the corresponding Tables, Nos. 1, 2, 3, 4, 5 and 6 discussed above were obtained with the use of a method for mechanically inducing increased osteoblast activity as illustrated in FIGS. 14A-14D. The method shown in FIGS. 14A-14D is provided only for the purpose of illustration, however, and the invention is not limited to the procedure(s) illustrated in the indicated Figures since a number of alternate techniques, which would be well known to those of ordinary skill in the art, may be used to obtain the necessary mechanical induction of osteoblast activity. Thus, in the representative method illustrated in FIGS. 14A-14D, Male Sprague Dawley rats, 9 weeks old, i.e., at a rapid growth stage, were housed for 5-10 days prior to surgery (bmx). On the day of surgery, the rats were weighed and anesthetized with a combination of ketamine (50 mg/kg) and xylazine (10 mg/kg) using a decapione. The anesthetic was prepared by combining 0.4-0.8 ml Ketamine with 0.5 ml. Xylazine and 8.5 ml saline. The rats were each injected with the anesthetic at the rate of 0.1 ml/10 g body weight.

In preparation for surgery, the hair over the left knee joint of each rat was shaved. The shaved area was prepped with Betadine scrub and then washed with ethanol. A longitudinal 1.0 cm. incision was then made across the medial aspect of the knee joint (see FIG. 14A). The knee was then bent and the incised tissue was pulled back to expose the patella tendon as a landmark. The patella was pushed aside and a 1.0 mm hole was drilled through the femoral intracondylar notch above the tendon by a smooth 0.035 k-wire drill bit into the marrow cavity (see FIG. 14B). The drilling motion was repeated 5 times. Subsequently, the above-described drilling step was repeated using a threaded 0.045 inches drill bit.

Once the hole was completed, the contents of the bone marrow cavity were back-flushed by injecting 5 ml of normal saline solution into the femur using a syringe attached to a 26-gauge needle (see FIG. 14C). As indicated above however, the ablation treatment may be carried out at any location on the bone, e.g., through the epiphysis, the midshaft portion, etc., at any angle, e.g, parallel to the shaft starting from the epiphysis, perpendicular to the bone at the midshaft, etc., and to any depth of penetration, according to the results which the treating physician desires to achieve, i.e, depending upon a particular application chosen for the technique.

The next step involved suturing the medial ligamentous structures with 4-0 Dexon thread and closing the skin incision with surgical metal clips (see FIG. 14D). Thereafter, each rat was injected with a 5 ml bolus of saline and tagged for identification. During recovery, the rate were given TYLENOL® brand acetaminophen solution (300 mg/kg/day) for the first 24 hours after surgery and then checked on a daily basis for the first 5 days.

On the day of sacrifice, each rat was euthanized in a $CO_2$ chamber. The rat's blood was then collected via a cardiac puncture. The femurs were removed and fixed in a 4% formalin solution, after which they were dehydrated in a graded series of ethanol solutions.

The bones were thereafter subjected to a variety of sample analysis techniques. These included X-ray analysis wherein the femurs were X-rayed in individually sealed plastic bags; PIXIMUS analysis using a Lunar PIXIMUS scanner to measure bone mineral density in the bone marrow cavity of the femurs; MicroCT analysis; and blood analysis for osteocalcin, PTH, CT, NTX and growth factors.

In one embodiment of the invention, the bone anabolic agent may be administered to the subject contemporaneous with the mechanical inducement of osteoblast activity (whether by increased osteoblast formation and/or by increased bone formation by pre-existing osteoblasts), which mechanical inducement may be achieved, e.g., by alteration of the bone marrow cavity. In preferred embodiments, marrow and/or other components of the marrow cavity is/are removed under pressure (e.g., by altering the relative pressure within versus without the marrow cavity).

In another embodiment the bone anabolic agent is administered subsequent to such mechanical inducement. In another embodiment the bone anabolic agent may be administered prior to mechanical inducement such that elevated levels of bone anabolic agent are already present at the time of mechanical inducement, which levels may then be maintained or continued intermittently for an extended period thereafter.

The bone anabolic agent may be administered orally, intravenously, intramuscularly, subcutaneously, via implant, transmucosally, transdermally, rectally, nasally, by depot injection or by inhalation and pulmonary absorption. In another embodiment the bone anabolic agent may be administered once as a time release formulation, a plurality of times, or over one or more extended periods. It is preferred that elevated blood levels of the anabolic agent be maintained at least intermittently for between about 14-365 days, and more preferably for between about 30-180 days, post-mechanical induction. Intermittent administration of parathyroid hormone, e.g., PTH[1-34]-$NH_2$, could occur once daily or once weekly resulting in peaks of blood concentration that return to baseline levels between doses, but nevertheless result in periodic elevated blood levels of a bone anabolic agent in a manner that overlaps the elevated osteoblast activity that is initially induced mechanically, although thereafter sustained, at least in part, by the anabolic agent.

In an additional embodiment the anabolic agent is selected from the group consisting of a parathyroid hormone (PTH), anabolic Vitamin D analogs, a low-density lipoprotein receptor-related protein 5 (LRP5), an activator of non-genomic estrogen-like signaling (ANGELS), a bone morphogenic protein (BMP), an insulin-like growth factor (IGF), a fibroblast growth factor (FGF), sclerostin, leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-$\beta 1$ and combinations thereof. As used herein, the term parathyroid hormone includes, but is not limited to natural parathyroid hormone, a truncate of natural parathyroid hormone, an amidated truncate of natural parathyroid hormone, an amidated natural parathyroid hormone and combinations thereof.

In one embodiment the bone anabolic agent is truncated PTH[1-34] in the free acid form. This material is commercially available in an FDA-approved pharmaceutical formulation from Eli Lilly & Co. under the trade mark FORTEO® (teriparatide). Other useful bone anabolic agents for use with the invention include, but are not limited to, an amidated truncate of natural parathyroid hormone, PTH[1-30]$NH_2$, PTH[1-31]$NH_2$, PTH[1-32]$NH_2$, PTH[1-33]$NH_2$, PTH[1-34]$NH_2$ and combinations thereof. In one preferred embodiment the bone anabolic agent is PTH[1-34]$NH_2$. Methods for the preparation of truncated parathyroid hormones are described in U.S. Pat. No. 6,103,495 to Mehta et al. Moreover, methodologies for amidating such truncated parathyroid hormones are provided in, for example, U.S. Pat. No. 5,789,234 to Bertelsen et al. and U.S. Pat. No. 6,319,685 to Gilligan et al. The contents of each of these patents is specifically incorporated herein by reference.

In one embodiment of the present method, a sufficient amount of the preferred truncated parathyroid hormone as discussed herein is administered to the subject to achieve, and thereafter maintain, a pulsatile blood concentration thereof in the subject of between about 50 and 350 pg/ml, preferably between about 100 and 200 pg/ml, and most preferably about 150 pg/ml. In another embodiment, the blood concentration of the parathyroid hormone in the subject is raised to its preferred level by no later than 7 days following mechanical alteration of the contents of the bone marrow cavity. As would be well known in this art, an appropriate dosage of the PTH bone anabolic agent must be calculated to achieve the above-indicated blood concentrations. In the case of injectable formulations, for example, the dose (in pure weight of the active hormone) given to, for example, a human subject, may be that taught in the literature relating to the bone anabolic activity of these various agents. Such dose may, but does not necessarily, range between about 10-200 μg, given once per day, more preferably between about 20-100 μg per dose and most preferably between about 20-50 μg per dose. Dosage levels of injectable formulations comprising bone anabolic agents other than the above-described parathyroid hormone-based agents would be consistent with those noted above for the PTH agents.

A series of experiments was performed comparing (1) lumbar vertebral bone mineral density, and (2) lumbar vertebral bone formation rate achieved with PTH[1-31]-$NH_2$ and PTH[1-34]-OH compared to the preferred PTH[1-34]-$NH_2$ analog discussed above in the absence of the mechanical induction step of the invention. The study involved a four-week treatment of female Sprague-Dawley rats at 10 months of age, and 6 months post-ovariectomy ("OVX"), which induces osteoporosis, with one of the three above-noted parathyroid hormone truncates. The rats were randomized into the following groups: sham OVX, OVX+vehicle, OVX+PTH [1-31]-$NH_2$ or PTH [1-34]-$NH_2$ (obtained from Unigene Laboratories, Inc.) at 2.5, 10 or 40 μg/kg/day subcutaneous, or PTH[1-34]-OH (obtained from Bachem) at 10 μg/kg/day subcutaneous. After 4 weeks of treatment, the right femur of each animal was analyzed by DEXA and bone histomorphometry. FIG. 15 is a bar graph providing a comparison of the lumbar vertebral bone mineral density achieved with PTH [1-31]-$NH_2$, PTH[1-34]-$NH_2$ and PTH[1-34]-OH. FIG. 16 is a bar graph comparing the lumbar vertebral formation rates achieved with these same truncates. Based on the results of these experiments it was determined that the bone anabolic activity of each of these analogs of PTH is substantially equivalent. Because of the similarity of anabolic action among the above-discussed parathyroid hormones, it is therefore reasonable to expect that all known PTH analogs will advantageously function in the desired manner in the method of the present invention.

In a further embodiment of the invention the mechanical induction of osteoblast activity is accomplished by inserting, into a bone marrow cavity of a bone targeted for enhanced bone formation, an object configured or adapted to physically alter the contents of the cavity and thereby to stimulate the osteoblast activity within the cavity. In another embodiment the mechanical alteration may include removal of at least a portion of the cavity contents.

In a still further embodiment, the method of the invention additionally comprises administering to the subject an antiresorptive agent for a time and at a concentration sufficient to substantially prevent resorption of the new bone produced due to the osteoblast activity. In one embodiment the antiresorptive agent may be administered contemporaneous with the administration of the bone anabolic agent. In another embodiment the antiresorptive agent is administered subsequent to the administration of the bone anabolic agent. In a further embodiment the administration of the antiresorptive agent may be commenced during administration of the bone anabolic agent and such administration may then be continued beyond the termination of administration of the bone anabolic agent.

In another embodiment of the invention a single agent may by administered having both bone anabolic and antiresorptive properties. Examples of such materials include, but are not limited to estrogen, strontium ranalate and selective estrogen receptor modulators (SERMS).

In an embodiment of the method of the invention the antiresorptive agent may be a calcitonin selected from the group consisting of human calcitonin, salmon calcitonin ("sCT"), eel calcitonin, elkatonin, porcine calcitonin, chicken calcitonin, calcitonin gene related peptide (CGRP) and combinations thereof. In a preferred embodiment the antiresorptive agent is salmon calcitonin. Blood levels of calcitonin, when used as the antiresorptive agent, preferably range between about 5-500 pg/ml, more preferably between about 10-250 pg/ml and most preferably 20-50 pg/ml. Moreover, human dosage levels of the subject calcitonin agents necessary to achieve the above blood levels, in the case of, e.g., injectable formulations, may be those taught in the literature relating to the use of these materials as anabolic agents. Such dose may, but does not necessarily, range between about 5-200 µg given once per day, more preferably between about 5-50 µg and most preferably 8-20 µg by weight of the pure drug, administered daily. Salmon calcitonin (sCT) administered by alternate routes, i.e., by nasal or oral administration, would require higher dosages than those discussed above.

Alternately, a variety of additional antiresorptive agents (i.e., other than the calcitonins) are useful with the method of the present invention. These include, generally, hormone replacement therapy (HRT) agents such as selective estrogen receptor modulators (SERMS), bisphosphonates, cathepsin-K inhibitors, strontium ranalate and various combinations thereof. Specific examples of additional antiresorptive agents include, but are not limited to, (1) PREMARIN® available from Wyeth Laboratories, which includes estrogen as the active ingredient. A typical accepted dosage is one 0.625 mg tablet daily; (2) ACTONEL® available from Proctor & Gamble, which includes, as its active ingredient, risedronate sodium. A typical accepted dosage is one 5 mg tablet daily or one 35 mg tablet weekly; (3) EVISTA® sold by Eli Lilly & Co. which includes raloxifene HCl as the active ingredient. A typical accepted dosage of this formulation is one 60 mg tablet taken daily; and (4) FOSAMAX® available from Merck Pharmaceuticals, which includes alendronate as the active ingredient. Typical dosages of this material are 10 mg/day or 70 mg/week.

The invention additionally provides a method for inducing bone formation within a bone of a subject which comprises mechanically altering the contents of a bone marrow cavity within a bone wherein such formation is to be induced to thereby stimulate, and thus increase osteoblast differentiation activity therein. The method further comprises administering to such subject an amount of an antiresorptive agent for a time and at a concentration sufficient to substantially prevent resorption of the new bone produced due to the osteoblast activity. The antiresorptive agent may be any of those identified above, but is preferably salmon calcitonin. It may be administered contemporaneous with the mechanical alteration of the marrow cavity and/or subsequent thereto. In this manner, the new bone growth attributable to the mechanical alteration treatment is substantially prevented from being resorbed. This method does not include the administration of a bone anabolic agent.

Except where otherwise noted or where apparent from the context, dosages herein refer to the weight of the active compounds unaffected by pharmaceutical excipients, diluents, carriers or other ingredients, although such other ingredients are typically included in the variety of dosage forms useful in the method of the invention. Any dosage form (i.e., capsule, tablet, injection or the like) commonly used in the pharmaceutical industry is appropriate for use herein and the terms "excipient", "diluent" or "carrier" include such non-active ingredients as are typically included, together with active ingredients, in the industry. For example, typical capsules, pills, enteric coatings, solid or liquid diluents or excipients, flavorants, preservatives, or the like are included. Moreover, it is additionally noted that with respect to all of the dosages recommended herein, the attending clinician should monitor individual patient response, and adjust the dosage accordingly.

The antiresorptive agent may be administered orally, intravenously, intramuscularly, subcutaneously, via implant, transmucosally, rectally, nasally, by depot injection, by inhalation and pulmonary absorption or transdermally. Moreover, the antiresorptive agent may be administered once, a plurality of times, or over one or more extended periods.

The invention additionally provides a method of inducing bone formation in a subject suffering from diminished bone mass which comprises the steps of targeting for treatment at least one bone of the subject, wherein each targeted bone defines a bone marrow cavity therein. The bone marrow cavity contains a quantity of bone marrow and a plurality of osteoblasts. The method of the invention further comprises mechanically altering the contents of the bone marrow cavity to thereby stimulate and thus increase osteoblast activity therein. Thereafter, bone mass is increased within the cavity due to the increased osteoblast activity. The method additionally comprises administering to the subject at least one bone anabolic agent for a duration and at a concentration sufficient to raise blood levels of the anabolic agent within the subject above natural levels thereof and thereby prolong the mechanically induced osteoblast activity. The method then further comprises additionally administering, either (1) contemporaneous with, (b) overlapping with, or (3) subsequent to the administration of the bone anabolic agent, an antiresorptive agent for a duration and at a concentration sufficient to substantially prevent resorption of new bone produced due to the increased osteoblast activity achieved in accordance with the invention. As with the method described above, the mechanical alteration of the contents of the bone marrow cavity thus permits specific bones of the subject to be targeted for enhanced bone formation.

In one embodiment of the above-described method the bone anabolic agent may be selected from the group consisting of natural parathyroid hormone, a truncate of natural parathyroid hormone, an amidated truncate of natural parathyroid hormone, an amidated natural parathyroid hormone and combinations thereof. In one particular embodiment, the agent may be PTH-[1-34] in the free acid form, sold by Eli Lilly & Co. under the trade mark FORTEO® (teriparatide). In a further embodiment the bone anabolic agent is an amidated truncate of natural parathyroid hormone and may be selected from among PTH[1-30]NH$_2$, PTH[1-31]NH$_2$, PTH[1-32]NH$_2$, PTH[1-33]NH$_2$, PTH[1-34]NH$_2$ and combinations thereof. A preferred choice for the bone anabolic agent is PTH[1-34]NH$_2$.

In a further embodiment of the invention a sufficient amount of an amidated truncate of natural parathyroid hormone is administered to the subject to achieve a pulsatile blood concentration thereof in the subject of between about 50 and 500 pg/ml, preferably between about 100-200 pg/ml and most preferably about 150 pg/ml. In the case of an injectable formulation, for example, the dose (in pure weight of the active hormone) given to a human subject, may be that taught in the literature relating to the bone anabolic activity of these various agents. Such dose may, but does not necessarily, range between about 10-200 µg per dose, more preferably between about 20-100 µg and most preferably between about 20-50 µg. When alternate delivery methods are used the dose may, but does not necessarily, range between about 10 µg-10 mg.

In a particular embodiment the antiresorptive agent is a calcitonin selected from among human calcitonin, salmon calcitonin, eel calcitonin, elkatonin, porcine calcitonin, chicken calcitonin gene related peptide (CGRP) and combinations thereof. In one embodiment the antiresorptive agent is salmon calcitonin. It is preferred to achieve blood levels of salmon calcitonin, when it is used as the antiresorptive agent, of between about 5-500 pg/ml, more preferably between about 10-250 pg/ml and most preferably between about 20-50 pg/ml. To achieve the above-indicated serum levels daily dosages of the antiresorptive agent used in, e.g., injectable formulations, may range between about 5-200 µg (pure weight of the drug), more preferably between about 5-50 µg and most preferably between about 8-20 µg. When alternate delivery methods, i.e., other than injection, are used, the dose may range between about 5 µg-5 mg. Administration of the antiresorptive agent preferably continues for at least 3 months and more preferably between 12-24 months.

One embodiment of the invention comprises the use of any of the above described methods to form a sufficient amount of additional bone in a jaw region of the subject to provide an anchor for a dental implant implanted therein. Alternately, or additionally, any of the methods described above may be utilized to form a sufficient amount of additional bone in one or more targeted bones of the subject to permit secure anchoring of a prosthetic device thereto. Such prosthetic devices may include, but are not limited to, a prosthetic knee, shoulder or hip. In a further embodiment, any of the methods of the invention may be utilized to form a sufficient amount of additional bone at any location in the subject to serve as a secure anchor for a hollow, adjustable insert anchored thereto. Additionally, any of the methods of the invention may be used in targeting at least one vertebra for additional bone formation, wherein a sufficient amount of bone is added to the at least one vertebra such that the subject is substantially freed from chronic pain caused due to vertebral crush.

In a still further embodiment the invention provides a kit for fostering bone formation in at least one targeted bone of a subject in need of such bone formation. The kit comprises at least one container having therein at least one bone anabolic agent and a mechanical alteration device for altering contents of a bone marrow cavity in at least one targeted bone of a subject. In another embodiment the kit may include at least one container having therein at least one bone anti-resorptive agent, as well as a mechanical alteration device for altering contents of the bone marrow cavity of a selected bone. In a still further embodiment, the kit may include multiple containers with at least one bone anabolic agent and at least one bone anti-resorptive agent, as well as the mechanical alteration device described above. In any event, the kit may additionally be provided with an evacuation device for evacuating at least a portion of the contents from the bone marrow cavity.

In one embodiment of the kit of the invention, the bone anabolic agent is selected from among natural parathyroid hormone, a truncate of natural parathyroid hormone, an amidated truncate of natural parathyroid hormone, an amidated natural parathyroid hormone, and combinations thereof. In a preferred embodiment the bone anabolic agent is a truncate of natural parathyroid hormone. A preferred truncate for use as the agent is PTH[1-34] in the free acid form. Other preferred truncates include amidated truncates. The bone anabolic agent may thus be selected from among PTH[1-30]NH$_2$, PTH[1-31]NH$_2$, PTH[1-32]NH$_2$, PTH[1-33]NH$_2$, PTH[1-34]NH$_2$ and combinations thereof. In a specific embodiment the bone anabolic agent is PTH[1-34]NH$_2$.

In an additional embodiment of the kit of the invention the antiresorptive agent is a calcitonin selected from the group consisting of human calcitonin, salmon calcitonin, eel calcitonin, elkatonin, porcine calcitonin, chicken calcitonin, calcitonin related gene peptide (CGRP) and combinations thereof. In a particular embodiment the antiresorptive agent is salmon calcitonin.

Although the present invention has been described in relation to particular embodiments thereof, many other variations and modifications and other uses will become apparent to those skilled in the art. The present invention, therefore, is not limited by the specific disclosure herein, but only by the claims.

What is claimed is:

1. A method of medical treatment producing a targeted increase in bone strength, form or volume in one or more bones of a subject in need thereof, the method comprising the steps of:
   (a) mechanically inducing an increase in osteoblast activity in said subject by a surgical treatment of one or more bones targeted for said increase; and
   (b) elevating blood concentration of at least one bone anabolic agent in said subject,
   wherein step (a) is performed no later than step (b) and in sufficient time proximity that the elevated concentration of said anabolic agent and said mechanically induced increase in osteoblast activity at least partially overlaps.

2. The method of claim 1, wherein the blood concentration of the bone anabolic agent is elevated by direct administration of a bone anabolic agent to said subject.

3. The method of claim 1, which further comprises providing said subject with an elevated blood concentration of at least one antiresorptive agent, wherein said elevated concentration is sufficient to substantially reduce resorption of new bone growth produced due to said increased osteoblast activity.

4. The method of claim 1 additionally comprising forming a sufficient amount of additional bone in a jaw region of said subject to provide an anchor for a dental implant implanted into said jaw region.

5. The method of claim 1 additionally comprising forming a sufficient amount of additional bone in one or more targeted bones of said subject to permit a prosthetic device implanted into at least one said targeted bone to be securely anchored thereto.

6. The method of claim 1, additionally comprising forming a sufficient amount of additional bone in said subject to serve as a secure anchor for a hollow, adjustable insert anchored to said additional bone.

7. The method of claim 1, which further comprises targeting at least one vertebra of said subject for additional bone formation and wherein a sufficient amount of bone is added to said at least one vertebra such that the subject is substantially freed from chronic pain caused due to vertebral crush.

8. The method of claim 1, wherein additional bone is formed on at least one vertebra of said subject in an amount sufficient to stabilize said at least one vertebra due to strengthening thereof.

9. The method of claim 1 wherein the mechanical induction of osteoblast activity is accomplished by inserting, into a bone marrow cavity of the one or more bones targeted for enhanced bone formation, an object configured or adapted to physically alter the contents of said cavity and thereby to stimulate said osteoblast activity within said cavity.

10. The method of claim 9, wherein said physical alteration further comprises removal of at least a portion of said altered cavity contents to provide additional room in the cavity for increased bone mass.

11. The method of claim 1 which further comprises: (c) administering to said subject an antiresorptive agent for a time and at a concentration sufficient to substantially reduce resorption of the new bone produced due to said osteoblast activity, wherein steps (b) and (c) are performed in any order, but in sufficient time proximity that said elevated concentration of said anabolic agent and said mechanically induced increase in osteoblast activity at least partially overlaps.

12. The method of claim 11, wherein administration of said antiresorptive agent is commenced during administration of the bone anabolic agent and continues beyond termination of said bone anabolic agent administration.

13. The method of claim 11, wherein the antiresorptive agent is administered orally, intravenously, intramuscularly, subcutaneously, via implant, transmucosally, rectally, nasally, by depot injection, by inhalation and pulmonary absorption or transdermally.

14. The method of claim 11, wherein the antiresorptive agent is a calcitonin selected from the group consisting of human calcitonin, salmon calcitonin, eel calcitonin, elkatonin, porcine calcitonin, chicken calcitonin, calcitonin gene related peptide (CGRP) and combinations thereof.

15. The method of claim 14, wherein the antiresorptive agent is salmon calcitonin and wherein the salmon calcitonin is administered to said subject in an amount calculated to achieve a substantially continuous blood concentration thereof of between about 5-500 pg/ml.

16. The method of claim 15, wherein the amount of said salmon calcitonin is from about 5 μg to 5 mg pure weight of the calcitonin per dose.

17. The method of claim 15, wherein the salmon calcitonin is administered via injection arid the amount of said salmon calcitonin is from about 5 μg-200 μg per dose.

18. The method of claim 1, wherein said at least one bone anabolic agent is selected from the group consisting of parathyroid hormone (PTH), anabolic Vitamin D analogs, a low-density lipoprotein receptor-related protein 5 (LRP5), an activator of non-genomic estrogen-like signaling (ANGELS), a bone morphogenic protein (BMP), an insulin-like growth factor (IGF), a fibroblast growth factor (FGF), sclerostin, leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-β1 and combinations thereof.

19. The method of claim 18, wherein the bone anabolic agent is CGRP.

20. The method of claim 18, wherein the bone anabolic agent is PTHrP.

21. The method of claim 18, wherein the bone anabolic agent is at least one parathyroid hormone selected from the group consisting of natural parathyroid hormone, a truncate of natural parathyroid hormone, an amidated truncate of natural parathyroid hormone, an amidated natural parathyroid hormone, and combinations thereof.

22. The method of claim 21, wherein the bone anabolic agent is selected from the group consisting of PTH[1-84] in the free acid form, PTH[1-84]NH$_2$, PTH[1-34] in the free acid form, PTH[1-30]NH$_2$, PTH[1-31]NH$_2$, PTH[1-32]NH$_2$, PTH[1-33]NH$_2$, PTH[1-34]NH$_2$ and combinations thereof.

23. The method of claim 21, wherein a sufficient amount of said parathyroid hormone is administered to said subject to achieve a pulsatile blood concentration thereof in said subject of between about 50-350 pg/ml.

24. The method of claim 23, wherein said sufficient amount of parathyroid hormone is from about 10 μg-10 mg pure weight of PTH hormone per dose.

25. The method of claim 23, wherein said parathyroid hormone is administered via injection and the sufficient amount of parathyroid hormone is from about 10-200 μg per dose.

26. The method of claim 23, wherein the blood concentration of said parathyroid hormone in said subject is raised to a level of between about 50-350 pg/ml by no later than 7 days following mechanical alteration of the contents of the bone marrow cavity.

27. A method of medical treatment producing a targeted increase in bone strength, form or volume in one or more bones of a subject need thereof, the method comprising the steps of:
  (a) mechanically inducing an increase in osteoblast activity in said subject by a surgical treatment of one or more bones targeted for said increase; and
  (b) administering to said subject at least one agent that causes elevated blood levels of an endogenous bone anabolic agent within said subject,
  wherein step (a) is performed no later than step (b) and in sufficient time proximity that the elevated concentration of said anabolic agent and said mechanically induced increase in osteoblast activity at least partially overlaps.

28. The method of claim 27, wherein the agent causing an increased expression of said endogenous bone anabolic agent within said subject is a calcilytic agent.

29. A method of medical treatment producing a targeted increase in bone strength, form or volume in one or more bones of a subject in need thereof comprising the steps of:
  (a) mechanically inducing an increase in osteoblast activity in said subject by a surgical treatment of one or more bones targeted for said increase; and
  (1) administering to said subject an antiresorptive agent for a time and at a concentration sufficient to substantially reduce resorption of new bone produced due to said osteoblast activity.

30. The method of claim 29, wherein the antiresorptive agent is administered orally, intravenously, intramuscularly, subcutaneously, via implant, transmucosally, rectally, nasally, by depot injection, by inhalation and pulmonary absorption or transdermally.

31. The method of claim 29, wherein the antiresorptive agent is a calcitonin selected from the group consisting of human calcitonin, salmon calcitonin, eel calcitonin, elkatonin, porcine calcitonin, chicken calcitonin, calcitonin gene related peptide (CGRP) and combinations thereof.

32. The method of claim 31, wherein the antiresorptive agent is salmon calcitonin and wherein the salmon calcitonin is administered to said subject in an amount calculated to achieve a substantially continuous blood concentration thereof of between about 5-500 pg/ml.

33. The method of claim 32, wherein the amount of said salmon calcitonin is from about 5 µg to 5 mg pure weight of the calcitonin per dose.

34. The method of claim 32, wherein the salmon calcitonin is administered via injection and the amount of said salmon calcitonin is from about 5 µg-200 µg per dose.

35. A method of medical treatment producing a targeted increase in bone strength, form or volume in one or more bones of a subject in need thereof, the method comprising the steps of:
(a) mechanically inducing an increase in osteoblast activity in said subject by a surgical treatment of one or more bones targeted for said increase; and
(b) elevating blood concentration of at least one bone anabolic agent in said subject,
wherein step (b) is performed no later than step (a) and in sufficient time proximity that the elevated concentration of said anabolic agent and said mechanically induced increase in osteoblast activity at least partially overlaps.

36. The method of claim 35, wherein the blood concentration of the bone anabolic agent is elevated by direct administration of a bone anabolic agent to said subject.

37. The method of claim 35, which further comprises providing said subject with an elevated blood concentration of at least one antiresorptive agent, wherein said elevated concentration is sufficient to substantially reduce resorption of new bone growth produced due to said increased osteoblast activity.

38. The method of claim 35 additionally comprising forming a sufficient amount of additional bone in a jaw region of said subject to provide an anchor for a dental implant implanted into said jaw region.

39. The method of claim 35 additionally comprising forming a sufficient amount of additional bone in one or more targeted bones of said subject to permit a prosthetic device implanted into at least one said targeted bone to be securely anchored thereto.

40. The method of claim 35, additionally comprising forming a sufficient amount of additional bone in said subject to serve as a secure anchor for a hollow, adjustable insert anchored to said additional bone.

41. The method of claim 35, which further comprises targeting at least one vertebra of said subject for additional bone formation and wherein a sufficient amount of bone is added to said at least one vertebra such that the subject is substantially freed from chronic pain caused due to vertebral crush.

42. The method of claim 35, wherein additional bone is formed on at least one vertebra of said subject in an amount sufficient to stabilize said at least one vertebra due to strengthening thereof.

43. The method of claim 35 wherein the mechanical induction of osteoblast activity is accomplished by inserting, into a bone marrow cavity of the one or more bones targeted for enhanced bone formation, an object configured or adapted to physically alter the contents of said cavity and thereby to stimulate said osteoblast activity within said cavity.

44. The method of claim 43, wherein said physical alteration further comprises removal of at least a portion of said altered cavity contents to provide additional room in the cavity for increased bone mass.

45. The method of claim 35 which further comprises: (c) administering to said subject an antiresorptive agent for a time and at a concentration sufficient to substantially reduce resorption of the new bone produced due to said osteoblast activity, wherein steps (b) and (c) are performed in any order, but in sufficient time proximity that said elevated concentration of said anabolic agent and said mechanically induced increase in osteoblast activity at least partially overlaps.

46. The method of claim 45, wherein administration of said antiresorptive agent is commenced during administration of the bone anabolic agent and continues beyond termination of said bone anabolic agent administration.

47. The method of claim 45, wherein the antiresorptive agent is administered orally, intravenously, intramuscularly, subcutaneously, via implant, transmucosally, rectally, nasally, by depot injection, by inhalation and pulmonary absorption or transdermally.

48. The method of claim 45, wherein the antiresorptive agent is a calcitonin selected from the group consisting of human calcitonin, salmon calcitonin, eel calcitonin, elkatonin, porcine calcitonin, chicken calcitonin, calcitonin gene related peptide (CGRP) and combinations thereof.

49. The method of claim 48, wherein the antiresorptive agent is salmon calcitonin and wherein the salmon calcitonin is administered to said subject in an amount calculated to achieve a substantially continuous blood concentration thereof of between about 5-500 pg/ml.

50. The method of claim 49, wherein the amount of said salmon calcitonin is from about 5 µg to 5 mg pure weight of the calcitonin per dose.

51. The method of claim 49, wherein the salmon calcitonin is administered via injection and the amount of said salmon calcitonin is from about 5 µg-200 µg per dose.

52. The method of claim 35, wherein said at least one bone anabolic agent is selected from the group consisting of parathyroid hormone (PTH), anabolic Vitamin D analogs, a low-density lipoprotein receptor-related protein 5 (LRP 5), an activator of non-genomic estrogen-like signaling (ANGELS), a bone morphogenic protein (BMP), an insulin-like growth factor (IGF), a fibroblast growth factor (FGF), sclerostin, leptin, a prostaglandin, a statin, strontium, a growth hormone, a growth hormone releasing factor (GHRF), hepatocyte growth factor (HGF), calcitonin gene related peptide (CGRP), parathyroid hormone related peptide (PTHrP), transforming growth factor (TGF)-β1 and combinations thereof.

53. The method of claim 52, wherein the bone anabolic agent is CGRP.

54. The method of claim 52, wherein the bone anabolic agent is PTHrP.

55. The method of claim 52, wherein the bone anabolic agent is at least one parathyroid hormone selected from the group consisting of natural parathyroid hormone, a truncate of natural parathyroid hormone, an amidated truncate of natural parathyroid hormone, an amidated natural parathyroid hormone, and combinations thereof.

56. The method of claim 55, wherein the bone anabolic agent is selected from the group consisting of PTH[1-84] in the free acid form, PTH[1-84]$NH_2$, PTH[1-34] in the free acid form, PTH[1-30]$NH_2$, PTH[1-31]$NH_2$, PTH[1-32]$NH_2$, PTH[1-33]$NH_2$, PTH[1-34]$NH_2$ and combinations thereof.

57. The method of claim 55, wherein a sufficient amount of said parathyroid hormone is administered to said subject to achieve a pulsatile blood concentration thereof in said subject of between about 50-350 pg/ml.

58. The method of claim 57, wherein said sufficient amount of parathyroid hormone is from about 10 μg-10 mg pure weight of PTH hormone per dose.

59. The method of claim 57, wherein said parathyroid hormone is administered via injection and the sufficient amount of parathyroid hormone is from about 10-200 μg per dose.

60. The method of claim 57, wherein the blood concentration of said parathyroid hormone in said subject is raised to a level of between about 50-350 pg/ml by no later than 7 days following mechanical alteration of the contents of the bone marrow cavity.

61. A method of medical treatment producing a targeted increase in bone strength, form or volume in one or more bones of a subject need thereof, the method comprising the steps of:
   (a) mechanically inducing an increase in osteoblast activity in said subject by a surgical treatment of one or more bones targeted for said increase; and
   (b) administering to said subject at least one agent that causes elevated blood levels of an endogenous bone anabolic agent within said subject,
   wherein step (b) is performed no later than step (a) and in sufficient time proximity that the elevated concentration of said anabolic agent and said mechanically induced increase in osteoblast activity at least partially overlaps.

62. The method of claim 61, wherein the agent causing an increased expression of said endogenous bone anabolic agent within said subject is a calcilytic agent.

* * * * *

UNITED STATES PATENT AND TRADEMARK OFFICE
CERTIFICATE OF CORRECTION

PATENT NO. : 7,648,965 B2 Page 1 of 1
APPLICATION NO. : 11/267987
DATED : January 19, 2010
INVENTOR(S) : Vignery et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 304 days.

Signed and Sealed this

Twenty-third Day of November, 2010

David J. Kappos
*Director of the United States Patent and Trademark Office*